(12) United States Patent
Ghisalba et al.

(10) Patent No.: US 6,235,516 B1
(45) Date of Patent: May 22, 2001

(54) BIOCATALYSTS WITH AMINE ACYLASE ACTIVITY

(75) Inventors: Oreste Ghisalba, Reinach (CH); Matthias Kittelmann, Freiburg; Kurt Laumen, March, both of (DE); Paula Walser-Volken, Ziefen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/171,646

(22) PCT Filed: Apr. 14, 1997

(86) PCT No.: PCT/EP97/01866

§ 371 Date: Nov. 12, 1998

§ 102(e) Date: Nov. 12, 1998

(87) PCT Pub. No.: WO97/41214

PCT Pub. Date: Nov. 6, 1997

(30) Foreign Application Priority Data

Apr. 25, 1996 (EP) .................................................. 96810266

(51) Int. Cl.[7] .............................. C12N 9/78; C12N 9/00; C12P 13/04; C07C 1/04
(52) U.S. Cl. ..................... 435/227; 435/183; 435/106; 435/228; 435/128; 435/280; 435/826; 435/893; 435/908
(58) Field of Search .................... 435/106, 227, 435/228, 128, 280, 826, 893, 908

(56) References Cited

U.S. PATENT DOCUMENTS

| | | | |
|---|---|---|---|
| 4,226,941 | 10/1980 | Goi et al. | 435/280 |
| 4,745,067 | 5/1988 | Umezawa et al. | 435/228 |
| 5,300,437 | 4/1994 | Stirling et al. | 435/280 |
| 5,360,724 | 11/1994 | Matcham et al. | 435/128 |
| 5,728,876 | 3/1998 | Balkenhohl et al. | 564/136 |

FOREIGN PATENT DOCUMENTS

| | | |
|---|---|---|
| 0 201 039 | 12/1986 | (EP) . |
| 0352846 * | 7/1989 | (EP) . |
| 0 399 589 | 11/1990 | (EP) . |
| 0 433 117 | 6/1991 | (EP) . |
| 2438054 | 4/1980 | (FR) . |
| 2246774 | 2/1992 | (GB) . |
| 06211847 | 8/1994 | (JP) . |
| WO 82 00253 | 2/1982 | (WO) . |

OTHER PUBLICATIONS

Derwent Abstracts 84–002847[01]—JP–A–58 198 296, Nov. 18, 1983.
Derwent Abstracts 84–092082 [15] (1984)—JP–A–59 039 294, Mar. 3, 1984.
Kameda, Y. et al., Chem. Pharm. Bull., vol. 26(9), pp. 2698–2704 (1978).
Ogawa J., et al., Bioorganic & Medicinal Chemistry, vol. 2, No. 6, pp. 429–432 (1994).
Shimizu, S. et al., Applied Microbiology Biotechnology, vol. 37, pp. 164–168 (1992).
Shimizu, S. et al., Eur. J. Biochem. vol. 209, pp. 375–382 (1992).

* cited by examiner

Primary Examiner—Ponnathapu Achutamurthy
Assistant Examiner—Manjunath Rao
(74) Attorney, Agent, or Firm—Gregory D. Ferraro

(57) ABSTRACT

The invention belongs to the field of biotechnology. It concerns a biocatalyst, i.e. a dead or living microorganism or a polypeptide, preferably in isolated form, which exhibits acylase enzymatic activity without lipase- or esterase-activity. The biocatalyst is capable of stereoselectively hydrolysing a racemic acylamide which has an aliphatic acyl residue and which is not a derivative of a natural amino acid.

8 Claims, No Drawings

BIOCATALYSTS WITH AMINE ACYLASE ACTIVITY

There is a high and continuous need for enantiomerically pure pharmaceutical and agrochemical drugs avoiding the side effects triggered by the therapeutically ineffective enantiomer. The present invention helps to fulfill this need by providing novel enzymes capable of stereoselectively hydrolysing a racemic acylamide.

Up to now enzymatic reactions on amines or amine-derivatives have been reported in the literature only for penicillins, cephalosporins, glucosamines, amino acids, and their derivatives. Among the known examples in this field figure the resolution of racemic 2-aminobutanol via the hydrolysis of appropriate N-acyl-derivatives by acylases of microbial origin (Japanese Kokai JP 58-198,296 and JP 59-39,294) and the enantiomeric enrichment of different amines possessing the amino group on a secondary carbon atom through a process involving the action of omega amino acid transaminases (Stirling et al., U.S. Pat. No. 5,300,437). In JP 06-253,875 the stereospecific transfer of the amino group of L-alanine to acetophenone in the presence of e.g. Acinetobacter sp. MBA-15 (FERM P-13432) for the production of S-1-phenyl ethylamine is disclosed. U.S. Pat. No. 5,360,724 discloses the production of optically active 1-aryl-2-amino propane by enantioselective transfer of the amino group in the racemate by means of amino acid transaminase from *Bacillus megaterium*. In DE 4332738 the production of optically active primary and secondary amines is disclosed; the process uses enantioselective acylation of a racemic amine with an activated ester as acyl donor in the presence of a hydrolase.

However, the present invention provides novel biocatalysts for enantioselective hydrolysis

OBJECT OF THE INVENTION

It is an object of the invention to provide novel biocatalysts for stereoselective hydrolysis of enantiomers in a racemic acylamide. Such biocatalysts are microorganisms capable of producing enzymes (acylases) capable of stereoselectively hydrolysing enantiomers in a racemic acylamide, or the enzymes themselves.

Moreover, it is an object to provide a process for the stereoselective hydrolysis of acylamides.

SUMMARY OF THE INVENTION

The invention concerns a biocatalyst, i.e. a dead or living microorganism or a polypeptide, preferably in isolated form, which exhibits acylase enzymatic activity without lipase- or esterase-activity. The biocatalyst is capable of stereoselectively hydrolysing a racemic acylamide which has an aliphatic acyl residue and which is not a derivative of a natural amino acid.

The invention accordingly also concerns microbial strains capable of producing an enzyme of the invention. Included are both genetically modified microorganisms and naturally occurring ones. The naturally occurring strains according to the invention are microorganisms obtainable by a selection process comprising inoculating a selection medium with a natural sample.

Another aspect of the invention is a process for the hydrolysis of a racemic N-acylamide which has an aliphatic acyl residue and which is not a derivative of a natural amino acid, characterized in that an enzyme according to the invention is used.

The process of the invention can be performed with free or immobilized enzyme, which can be used in enriched or purified form or in the form of a crude cell extract. In another embodiment of the invention a microorganism expressing an acylase of the invention is used for performing the reaction, i.e. the enzyme is in cell-bound form.

The process of the invention can be used for separating racemates, if one stereoisomer of the racemic acyl amide is specifically hydrolyzed. However, if the hydrolysis is not stereoselective (e.g. since the acylamide is not a racemate or since the enzyme hydrolyses both enantiomers of a certain racemic acylamide), the process of the invention can also be used for other purposes, e.g. in the chemistry of protecting groups.

DETAILED DESCRIPTION OF THE INVENTION

The invention concerns a biocatalyst exhibiting amine acylase enzymatic activity without lipase- or esterase-activity, which biocatalyst is capable of stereoselectively hydrolysing a racemic acylamide of formula (1)

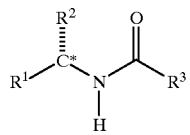

(1)

wherein $R^2$ is aryl or $C_1$–$C_4$aryl; or $R^1$ and $R^2$ together are forming a 5 to 7 membered ring substituted by or fused to aryl;

$R^3$ is an aliphatic acyl residue; and $R^1$ and $R^3$ together are chosen in order to form a compound of formula (1) that is not a derivative of a natural amino acid; wherein each of the residues can be substituted or unsubstituted.

A preferred embodiment is a biocatalyst, the substrate of which can be hydrolyzed to a primary amine. The biocatalyst according of the invention is preferably selected from the group of (a) a polypeptide with said enzymatic activity and (b) a living microorganism or dead microorganism containing a polypeptide with said enzymatic activity or a cell extract of such a microorganism. A dead microorganism in context with the present invention is e.g. a microorganism in a disintegrated form in which the cell wall and/or cell membrane is mechanically or chemically disrupted or removed.

The term without lipase- or esterase-activity in context with the present invention means that no enzymatic activity can be detected in the Api Zym Test (Bio Mérieux SA, Marcy-L'Etoile, France). In this test the C4 esterase activity is tested with 2-naphtyl butyrate, C8 esterase activity with 2-naphtyl caproate, and C14 lipase activity with 2-naphtyl myristate.

In particular, the invention concerns a enzyme with amine acylase activity and without lipase- or esterase-activity and mutants, variants, and fragments of said acylase, which exhibit acylase activity and without lipase- or esterase-activity. A preferred embodiment is a polypeptide, the substrate of which can be hydrolyzed to a primary amine.

The polypeptide of the invention is herein also named "acylase of the invention" or "enzyme of the invention". If not stated otherwise, all these terms include not only the naturally occurring, authentic sequence of a polypeptide of the invention, which are the preferred embodiments of the invention, but also all mutants, variants and fragments thereof which exhibit acylase enzymatic activity, preferably the same stereoselective activity as the natural enzyme. The polypeptide of the invention can be used in enriched or, preferably, purified form.

In a preferred embodiment of the invention a polypeptide of the invention is particularly capable of catalyzing the following stereoselective reaction (A)

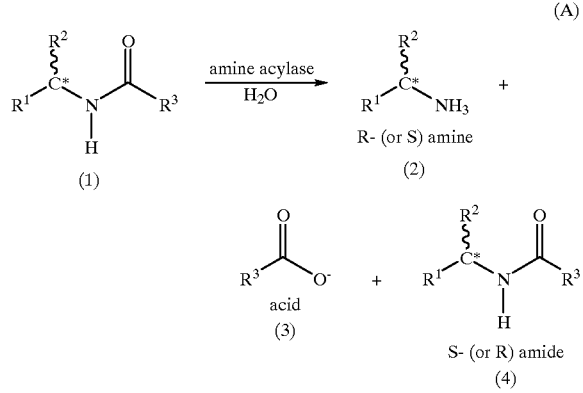

wherein the racemic acylamide of the formula (1) is stereoselectively hydrolyzed with an amine acylase of the invention, which is a polypeptide with amine acylase enzymatic activity but without lipase- or esterase-activity, and which is capable of stereoselectively hydrolysing the racemic acylamide of formula (1), and wherein said hydrolysis results in the R- (or S-) amine of the formula (2) and the acid of formula (3) and the S- (or R-) amide of formula (4), whereby
whereby in the formula (1) to (4)

$R^1$ is hydrogen, $C_1$–$C_8$alkyl, $C_2$–$C_8$alkenyl, $C_1$–$C_8$alkoxy, $C_2$–$C_8$alkylcarboxy or carboxy; preferably $C_1$–$C_4$alkyl, $C_2$–$C_4$alkenyl, $C_1$–$C_4$alkoxy or $C_2$–$C_4$alkylcarboxy; more preferably $C_1$–$C_3$alkyl, $C_2$–$C_3$alkenyl, $C_1$–$C_3$alkoxy or $C_2$–$C_3$alkylcarboxy; and most preferably selected from the group consisting of hydrogen, methyl, ethyl, n-propyl, iso-propyl, propyl-1-en, propyl-2-en, prop-2-ylen, and methoxy;

$R^2$ is aryl or $C_1$–$C_4$aryl; unsubstituted or substituted by $C_1$–$C_4$alkyl, $C_1$–alkoxy, $C_1$–$C_4$hydroxyalkyl, $C_1$–$C_4$aminoalkyl, $C_1$–$C_4$haloalkyl, hydroxy, amino, halogeno, nitro, sulfo, or cayno;

or wherein $R_1$ and $R_2$ together are forming a 5 to 7 membered ring substituted by or fused to aryl, wherein the rings may contain one or two heteroatoms selected from nitrogen, sulfur and oxygen; preferably indane, tetraline or chromane, unsubstituted or substituted with methoxy, ethoxy, halogeno, methyl, ethyl, nitro, cyano, amino, hydroxy, trifluoromethyl; and $R^3$ is an aliphatic acyl residue; preferably $C_1$–$C_4$alkyl; and more preferably methyl.

Aryl is, for example a homo- or heterocyclyl. A suitable ring systems is, for example, a single or double ring system having from 3 to 10 ring atoms, is bonded via a carbon atom or via a nitrogen atom and contains up to 4 hetero atoms selected from oxygen, nitrogen, sulfur, and sulfur linked to 1 or 2 oxygen atoms; which in addition may also be fused with 1 or 2 phenyl radicals or with 1 or 2 cycloalkyl radicals, cycloalkyl preferably having from 5 to 7 ring atoms; and which may be unsaturated or partially or fully saturated.

Examples for aryl are phenyl, napthyl, biphenylyl, anthryl, fluorenyl, thienyl, furyl, pyrrolyl, imidazolyl, pyrazolyl, oxazolyl, thiazolyl, tetrazolyl, pyridyl, pyrazinyl, pyrimidinyl, pyridazinyl, indolyl, benzimidazolyl, quinolyl, isoquinolyl, 3,1-benzofuranyl, chromanyl, cyclohexa[b]pyrrolyl, cyclohexa[b]pyridyl, [b]pyrimidinyl, pyrrolidinyl, pyrrolinyl, cyclohexa[b]pyrazinyl, cyclohexa[b]pyrimidinyl, imidazolidyl, piperidyl, piperazinyl, morpholinyl, thiomorpholinyl, S,S-dioxo-thiomorpholinyl, indolinyl, isoindolinyl, 4,5,6,7-tetrahydro indolyl, 1,2,3,4-tetrahydroquinolyl or 1,2,3,4-tetrahydroisoquinolyl, for example one of the last-mentioned radicals, being unsubstituted or substituted by one or more substituents selected from lower alkyl, for example methyl, phenyl, 1- or 2-naphthyl, phenyl-lower alkyl, for example benzyl, hydroxy-lower alkyl, for example hydroxymethyl or 2-hydroxyethyl, hydroxy, lower alkoxy, for example methoxy or ethoxy, amino, lower alkylamino, for example methyl-, ethyl- or tert-butyl-amino, di-lower alkylamino, for example dimethyl- or diethyl-amino, carboxy, lower alkoxycarbonyl, for example methoxy-, isopropoxy-, sec-butoxy- or tert-butoxy-carbonyl, phenyl- or naphthyl-lower alkoxycarbonyl, for example benzyloxycarbonyl, halogen, for example fluorine, chlorine, bromine or iodine, especially chlorine or bromine, lower alkanoyl, for example acetyl or pivaloyl, nitro, oxo and/or by cyano.

In a preferred embodiment aryl is unsubstituted or substituted by one or more substituents selected from methyl, hydroxymethyl, 2-hydroxyethyl, hydroxy, methoxy; ethoxy, amino, methyl-amino, ethyl-amino, tert-butyl-amino, dimethylamino, diethyl-amino, carboxy, methoxy-carbonyl, isopropoxy-carbonyl, sec-butoxy-carbonyl, tert-butoxy-carbonyl, fluorine, chlorine, bromine, acetyl or pivaloyl, nitro, oxo and/or by cyano.

In a preferred embodiment of the above reaction A, a racemic acylamide is hydrolyzed wherein $R^3$ is $C_1$–$C_3$alkyl, more preferably $C_1$alkyl. In particular, if an acylase obtainable from *Rhodococcus globerulus* or *Rhodococcus equi* is used, $R^3$ is most preferably $C_1$–$C_3$alkyl; if an acylase obtainable from *Arthrobacter aurescens* is used, $R^3$ is most preferably $C_1$alkyl.

The term 'substituted' means that the moiety in question can be substituted by one to three identical or different substituents, preferably one or two identical or different, most preferably by one substituent selected from the group consisting of $C_1$–$C_8$alkyl (preferably methyl), haloalkyl (preferably trifluoromethyl), halogen (preferably fluorine or chlorine), amino, nitro, and $C_1$–$C_8$alkoxy (preferably methoxy).

In accordance with the present invention aryl standing alone or being member or an aralkyl moiety is a carbocyclic radical in which at least one ring is in the form of a 6-membered aromatic ring (i.e. a benzene ring). Preferred are phenyl, naphthyl, such as 1- or 2-naphthyl, biphenylyl, such as, especially, 4-biphenylyl, anthryl, and fluorenyl, and also such ring systems having one or more fused saturated rings.

In a preferred embodiment aralkyl stands for an aliphatic radical substituted by an aryl moiety, wherein the aliphatic radical is an unbranched or branched $C_1$–$C_8$alkylene (preferably $C_1$–$C_3$alkylene, most preferably methylene or ethylene) and the aryl moiety is a carbocyclic radical as defined above. In a more preferred embodiment aralkyl stands for a radical of the formula 10, 11 or 12

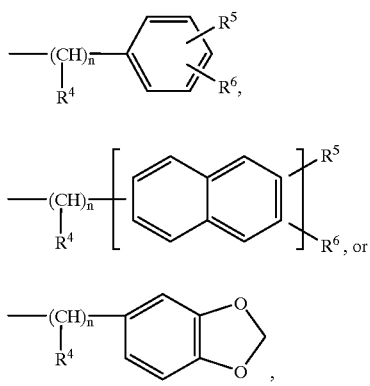

(10)

(11)

(12)

wherein

R⁴ is hydrogen or $C_1$–$C_4$alkyl; preferably hydrogen or methyl; more preferably hydrogen;

n is an integral number selected from 0, 1, 2, 3 and 4; preferably 0, 1, 2 and 3; more preferably 0, 1 and 2;

R⁵ and R⁶ are each independent of each other hydrogen, $C_1$–$C_4$alkyl, $C_1$–$C_4$haloalkyl, halogeno, amino, cyano, nitro or $C_1$–$C_4$alkoxy; preferably hydrogen, methyl, ethyl, trifluoromethyl, fluorine, chlorine, bromine, iodine, amino, nitro, cyano or methoxy; more preferably hydrogen, methyl, fluorine, chlorine, cyano, nitro or methoxy.

Further preferred compounds are of formula 13, 14 and 15

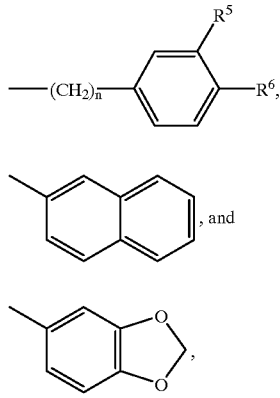

(13)

(14)

(15)

wherein n is an integral number selected from 0, 1 and 2; R⁵ and R⁶ are each independent of each other hydrogen or cyano.

Further preferred compounds are of formulae 16 and 17

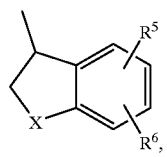

(16)

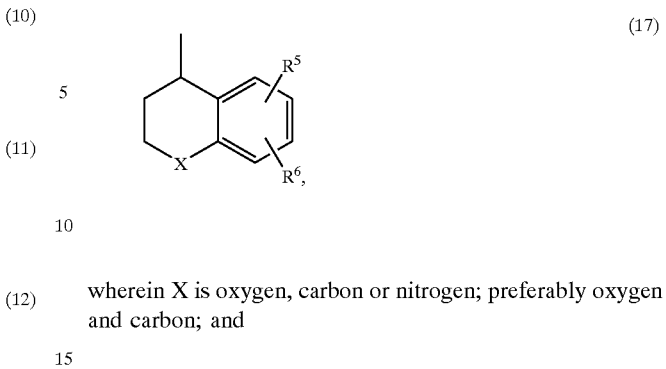

(17)

wherein X is oxygen, carbon or nitrogen; preferably oxygen and carbon; and

R⁵ and R⁶ are each independent of each other hydrogen, $C_1$–$C_4$alkyl, $C_1$–$C_4$haloalkyl, halogeno, amino, cyano, nitro or $C_1$–$C_4$alkoxy; preferably hydrogen, methyl, ethyl, iodo, bromo, trifluoromethyl, chloro, fluoro, amino, cyano, nitro, methoxy or ethoxy.

If R¹ and R² form together an unsubstituted or substituted cyclic heteroaliphatic radical said radical preferably stands for a compound of formula (18)

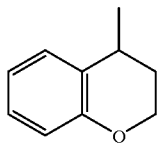

(18)

Further examples for suitable compounds are:

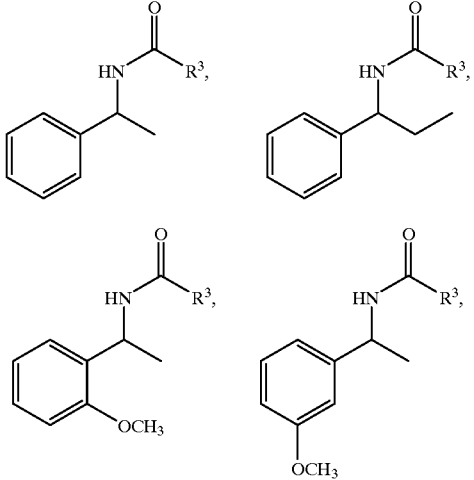

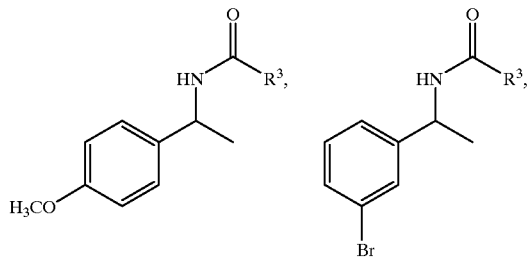

-continued
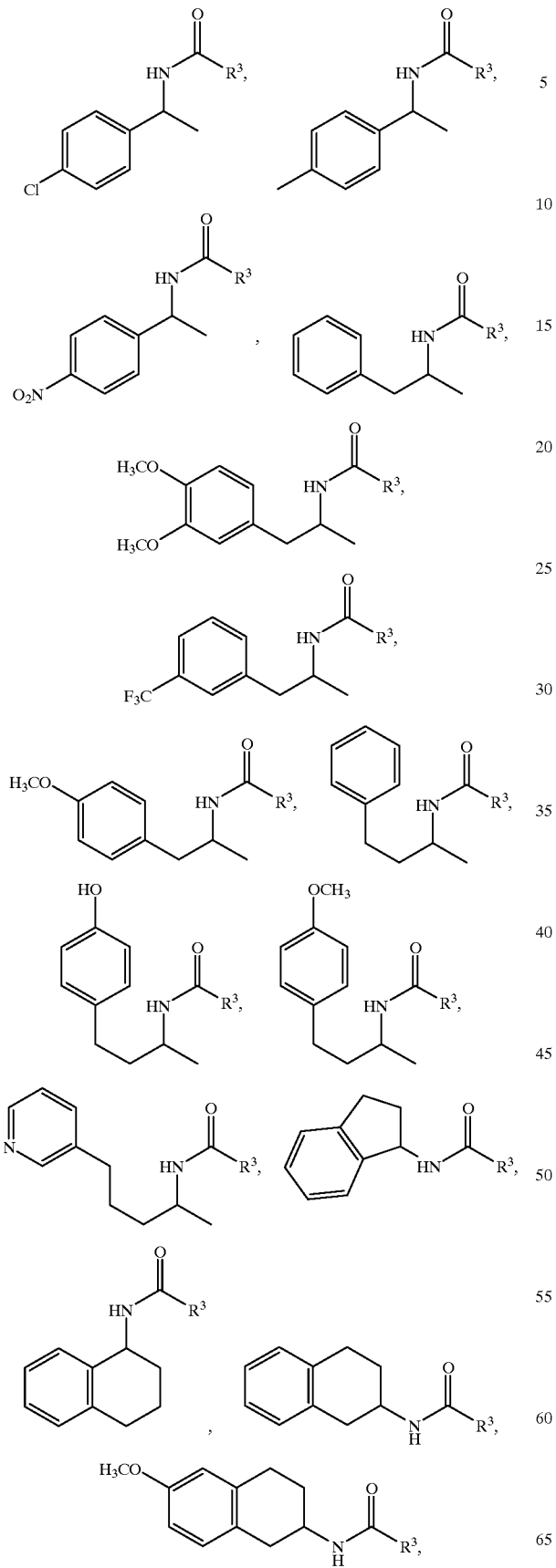
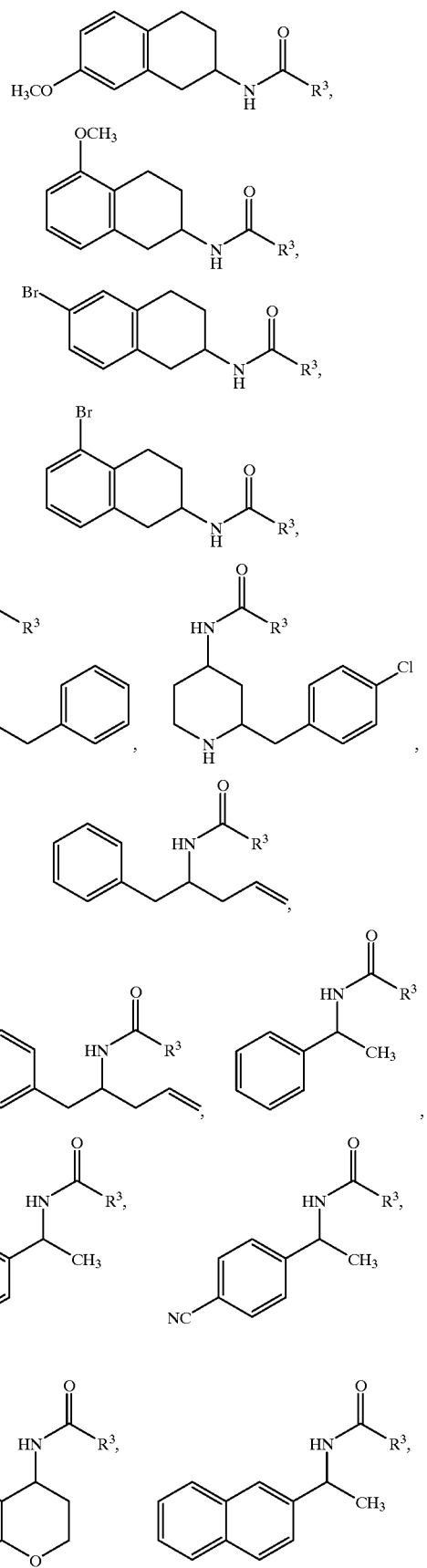

-continued

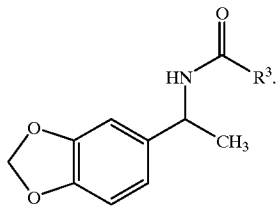

An acylase of the invention is obtainable from a microorganism selectable by a process comprising inoculating a selection medium with natural samples such as soil, water, or plant silage, said selection medium comprising an acylamide as sole carbon source. The acylamide can be used as racemate or, if a preselection on a R- or S-enantiomer specific acylase is intended, as R- or S-enantiomer. In the preferred embodiments of the selection process, the acylamides described above in context with the hydrolysis reaction are used for the selection.

Apart from the carbon source, the selection medium also contains all essential ingredients necessary for allowing growth of microorganisms, such as mineral salts, N-sources, and trace elements.

In the most preferred embodiments, the selection medium comprises an acylamide selected from the group consisting of N-acetyl-1-phenylethylamine as racemate or S- or R-enantiomer and N-acetyl-2-amino-1-phenyl-4-pentene as racemate or S- or R-enantiomer.

A suitable selection medium used for performing the invention comprises 3 g of the acylamide and further contains 3 ml trace element solution SL-6, and 1 l mineral salt solution ML1 (pH 7.0), whereby the composition of the mineral salt solution ML1 is 5 g $K_2HPO_4$, 0.2 g $MgSO_4 \times 7H_2O$, 20 mg $CaCl_2$, 20 mg $FeSO_4 \times 7H_2O$, 1.5 g $(NH_4)_2SO_4$, and 1 l Aqua deion (pH 7.0); and the composition of the trace element solution SL-6 is 20 mg $NiCl_2 \times 6H_2O$, 200 mg $CoCl_2 \times 6H_2O$, 30 mg $MnCl_2 \times 4H_2O$, 10 mg $CuCl_2 \times 2H_2O$, 300 mg $H_3BO_3$, 30 mg $Na_2MoO_4 \times 2H_2O$, 100 mg $ZnSO_4 \times 7H_2O$, and 1 l Aqua deion. This recipe, however, may of course be varied as long as sufficient trace elements, mineral salts and N-source are provided.

Preferably, an acylase of the invention is obtainable from a microorganism selected from the group consisting of *Rhodococcus globerulus*, *Rhodococcus equi*, and *Arthrobacter aurescens*, more preferably from a microorganism selected from the group consisting of *Rhodococcus globerulus* K1/1, DSM 10337, *Rhodococcus equi* Ac6, DSM 10278, and *Arthrobacter aurescens* AcR5b, DSM 10280.

The term biocatalyst according to the present invention also includes living or dead microorganisms exhibiting the enzymatic activity of an acylase of the invention. Accordingly, the invention also concerns a microorganism expressing an acylase of the invention. Included are both genetically modified microorganisms and naturally occurring ones. While the former can be produced either by mutation or by genetic engineering, i.e. by transforming a microorganism such as bacteria, e.g. *E. coli*, or a yeast, e.g. Hansenula or Saccharomyces, with a gene coding for an acylase of the invention, the latter is obtainable from natural sources by a selection process comprising inoculating a selection medium with natural samples, e.g. soil, water, plant silage.

A gene coding for an acylase of the invention can, for example, be obtained by identifying at least a part of the sequence of an isolated acylase of the invention, deducing DNA sequences coding for the partial protein sequence, preparing an oligonucleotide or a mixture of oligonucleotides (taking into consideration the degeneracy of the genetic code), probing a DNA library derived from the microbial strain naturally expressing the desired acylase, isolating the gene, and cloning it into a suitable vector for transformation of the microorganism to be genetically modified. In another approach, the full sequence of the isolated acylase can be determined and a DNA coding the protein can be produced synthetically. It is also very easily possible to screen a suitable DNA library in *E. coli*, for example, for growth on the corresponding amide as sole carbon source in order to obtain a transformed clone expressing the acylase.

A naturally occurring microorganism having acylase activity can be obtained by a process outlined hereinafter and can be converted by mutation in a manner known per se, for example using generally known mutagens, such as UV-rays or X-rays, or mutagenic chemicals, into mutants that are differentiated from their parents by improved properties, e.g. lower nutrient medium demands, higher growth rates and, especially, higher acylase activity. Such mutants can also occur spontaneously. The identification and isolation of such mutants is carried out also in a manner known per se: the acylase activity of colonies of such mutants is ascertained, for example, after disintegration of the cells, by adding specific amounts of a suitable acylamide substrate to aliquot portions of the cell residue and qualitatively or quantitatively determining the reaction products that are formed by means of chromatography, especially HPLC.

Isolation of a microorganism naturally expressing an acylase of the invention can be achieved by a selection process comprising inoculating a selection medium with natural samples such as soil, water, or plant silage, said selection medium comprising an acylamide as sole carbon source. The acylamide can be used as racemate or, if a preselection on a R- or S-enantiomer specific acylase is intended, as R- or S-enantiomer. In the preferred embodiments of the selection process, the acylamides described above in context with the hydrolysis reaction are used for the selection.

Apart from the carbon source, the selection medium also contains all essential ingredients necessary for allowing growth of microorganisms, such as mineral salts, N-sources and trace elements.

In the most preferred embodiments, the selection medium comprises an acylamide selected from the group consisting of N-acetyl-1-phenylethylamine as racemate or S- or R-enantiomer and 2-amino-1-phenyl-4-pentene as racemate or S- or R-enantiomer.

A suitable selection medium used for performing the invention comprises 3 g of the acylamide and further contains 3 ml trace element solution SL-6, and 1 l mineral salt solution ML1 (pH 7.0), whereby the composition of the mineral salt solution ML1 is 5 g $K_2HPO_4$, 0.2 g $MgSO_4 \times 7H_2O$, 20 mg $CaCl_2$, 20 mg $FeSO_4 \times 7H_2O$, 1.5 g $(NH_4)_2SO_4$ and 1 l Aqua deion (pH 7.0); and the composition of the trace element solution SL-6 is 20 mg $NiCl_2 \times 6H_2O$, 200 mg $CoCl_2 \times 6H_2O$, 30 mg $MnCl_2 \times 4H_2O$, 10 mg $CuCl_2 \times 2H_2O$, 300 mg $H_3BO_3$, 30 mg $Na_2MoO_4 \times 2H_2O$, 100 mg $ZnSO_4 \times 7H_2O$, and 1 l Aqua deion. This recipe, however, may of course be varied as long as sufficient trace elements, mineral salts, and N-source are provided.

A preferred microorganism is selected from the group consisting of *Rhodococcus globerulus*, *Rhodococcus equi*, and *Arthrobacter aurescens*, more preferably selected from the group consisting of *Rhodococcus globerulus* K1/1, DSM 10337, Rhodococcus equi Ac6, DSM 10278, and *Arthrobacter aurescens* AcR5b, DSM 10280.

The acylase is isolated from the microorganism by methods well known in the art, in particular by the methods described in the examples.

Preferred is a substantially purified biocatalyst according to claim 1, isolated from a microorganism as defined above; more preferably comprising an amino acid sequence selected from the group consisting of SEQ ID NOs 1, 2, 3 and 4.

An important aspect of the invention relates to a process comprising the hydrolysis of a racemic N-acylamide which has an aliphatic acyl residue and which is not a derivative of a natural amino acid, characterized in that an acylase of the invention is used. The process comprises reaction A shown above. In the preferred embodiments of the process, residues $R^1$, $R^2$, and $R^3$ and the acylase have the meanings outlined above. In the case of the acylases of *Rhodococcus globerulus* K1/1, DSM 10337 or *Rhodococcus equi* Ac6, DSM 10278, $R^1$ can also be urea.

The process of the invention (see process A above) can be performed with any "biocatalyst" having the activity of an enzyme of the invention. A "biocatalyst" according to the invention is, for example, a microorganism expressing an acylase of the invention, for example a naturally occurring, a mutated or a recombinant microorganism defined above, a crude cell extract of such a microorganism, an enriched or a purified enzyme according to the invention. The term microorganism in this context includes the living microorganism or the dead microorganism, e.g. in a disintegrated form in which the cell wall and/or cell membrane is mechanically or chemically disrupted or removed.

A "biocatalyst" for use in a process of the invention may be immobilized. The immobilization of said "biocatalyst" can be carried out analogously to processes known per se, e.g. coupling to a solid support or enclosing in an enzyme membrane reactor.

A microorganism expressing acylase enzyme activity can be either a naturally occurring one, optionally converted by mutation as described above, or a microorganism transformed by genetic engineering techniques with a gene coding for an acylase of the invention to be able to produce the desired acylase. The hydrolysis of the acylamide substrate with microbial cell extract is preferably carried out in homogeneous aqueous solution at pH 5 to 10.5, more preferably at pH 6 to 9.5. For the stabilization of the pH value, the reaction is carried out in a manner known per se in buffered solution or using a pH-stat. The reaction temperature is approximately from 10 to 65° C., more preferably from 20 to 50° C., even more preferably from 20 to 30° C. The acylamide substrate is used preferably in a concentration of 1 mM to 1 M, more preferably 10 mM to 100 mM. However, if the substrate is less soluble, it is also possible to use a substrate suspension.

The enzymes isolated from *Rhodococcus equi* Ac6, DSM 10278, and *Arthrobacter aurescens* AcR5b, DSM 10280, differ in the pH and temperature optimum. For the enzyme of *Rhodococcus equi* Ac6, DSM 10278, the preferred pH range is 5 to 10.5, more preferred is 6 to 8, even more preferred is 6.5 to 7.5, and the preferred temperature range is 10 to 65° C., more preferred is 20 to 37° C., even more preferred is 25 to 30° C. For the enzyme of *Arthrobacter aurescens* AcR5b, DSM 10280, the preferred pH range is 5.5 to 10.5, more preferred is 7 to 9.5, and the preferred temperature range is 10 to 65° C., more preferred is 45 to 50° C. (if maximal activity is desired) or 20 to 30° C. (if maximal enzyme stability is desired).

The process according to the invention can be carried out either as a batch process or continuously in an enzyme membrane reactor (EMR). In the latter case, the enzyme membrane reactor is preferably fitted with an ultrafiltration membrane having a separation limit of less than approximately 30 000, so that the enzymes contained in the reaction mixture are held back whilst the low-molecular-weight products and unreacted reactants pass through the membrane and the product can be isolated from the outflow. The reactor is preferably sterilized before use so that the addition of antibacterial substances can be dispensed with. The reactions are carried out in a manner analogous to that described above.

The process according to the invention can also be carried out by percolating the solution containing the acylamide substrate, which has been adjusted to a suitable pH value, through a solid carrier on which the acylase contained in the crude microbial extract has been immobilized (the matrix-bound enzyme preparation is obtainable, for example, by percolation of the crude microbial extract through CNBr-activated Sepharose, eupergite or the like).

Working up the reaction mixture and purification of the products and unhydrolyzed reactants or the unhydrolyzable enantiomer in accordance with the invention are carried out by customary processes known from the State of the Art. For example, the reaction mixture can be clarified by filtration or, preferably, centrifugation, and then the enzyme can be separated by ultrafiltration (membrane with separation limit of <30 000 Daltons) and the remaining product can be washed out of the retentate by diafiltration. The actual purification is then carried out, for example, by chromatographic methods, e.g. gel chromatography (inter alia Sephadex G-25), ion exchange chromatography, e.g. anion exchange chromatography, thin layer chromatography, HPLC or the like. Selective extraction of amide is performed, e.g., preferably at low pH values and after that the amine can be extracted at preferably alkaline pH values.

In order to obtain the cell extract used in accordance with the process, a microorganism having acylase activity, especially one of those mentioned above, is cultivated in an aqueous nutrient medium that contains assimilable carbon and nitrogen sources and also mineral salts, at a pH value of approximately from 6 to 9, preferably of approximately from the biomass is removed and the cell extract is obtained. The fermentation time is so selected that optimum titers with respect to acylase activity are achieved.

When the cell density has reached an adequate value, the cultivation is discontinued. The culture broth is separated off in known manner, e.g. by centrifugation, and the sedimented cells are broken down in customary manner, e.g. by shaking with fine glass beads, by ultrasound treatment, or using a French press. Insoluble cell components and, if used, glass beads, are removed, e.g., by centrifugation, and the residue is used as the enzyme source (crude extract). The residue, as an acylase-containing crude extract, can be used directly in the process according to the invention. Advantageously, however, in order to remove nucleic acids (viscous solutions!) the crude extract is treated with a polycationic agent, e.g. polyethyleneimine, a polyamine such as spermidine, streptomycin-sulfate, or ribonuclease or $Mn^{2+}$ salts, and the precipitated nucleic acids are removed by centrifugation.

Preferably, the crude cell extract is subjected to one or more conventional purification steps in order to remove interfering components from the extract.

The process of the invention can be used for separating racemates, if one stereoisomer of the racemic acyl amide is specifically hydrolyzed. However, if hydrolysis is not stereoselective (e.g. since the acylamide is not a racemate or since the enzyme hydrolysis both enantiomers of a certain racemic acylamide), the process of the invention can be used in the chemistry of protecting groups. In this case, the C-atom to which $R^2$ and $R^3$ are bound in the substrates need not be chiral. In this case, 100% of the substrate can be hydrolyzed. In one example, $R^2$ and $R^3$ are connected covalently to form a benzene ring; in another example, $R^2$ and $R^3$ are connected covalently to form a cyclopentane ring fused with benzene. In both cases, $R^1$ is preferentially methyl.

The following examples are illustrative, however, should not be construed to limit the present invention.

EXAMPLES

Example 1

Isolation of Microorganisms with (S)-1-phenylethylamine Acylase Activity 16 soil samples are suspended in the mineral salt solution ML1 described below, which has been sterilized before by autoclavation at 120° C. for 20 min. 0.1 ml of these solutions and 12 water samples from nature and from a sewage purification plant are used for the inoculation of 4 ml of liquid medium (=enrichment medium). In parallel control cultures with enrichment medium not containing racemic N-acetyl-1-phenylethylamine are inoculated. The composition of the mineral salt solution ML1 is:

| | | |
|---|---|---|
| $K_2HPO_4$ | 5.0 | g |
| $MgSO_4 \times 7H_2O$ | 0.2 | g |
| $CaCl_2$ | 20 | mg |
| $FeSO_4 \times 7H_2O$ | 20 | mg |
| $(NH_4)_2SO_4$ | 1.5 | g |
| Aqua deion. | 1.0 | l |
| pH-value | 7.0 | |

| | | |
|---|---|---|
| Racemic N-acetyl-1-phenylethylamine | 3.0 | g |
| Trace element solution SL-6 | 3.0 | ml |
| Mineral salt solution ML1 | 1.0 | l |
| pH | 7.0 | |

| | | |
|---|---|---|
| $NiCl_2 \times 6H_2O$ | 20 | mg |
| $CoCl_2 \times 6H_2O$ | 200 | mg |
| $MnCl_2 \times 4H_2O$ | 30 | mg |
| $CuCl_2 \times 2H_2O$ | 10 | mg |
| $H_3BO_3$ | 300 | mg |
| $Na_2MoO_4 \times 2H_2O$ | 30 | mg |
| $ZnSO_4 \times 7H_2O$ | 100 | mg |
| Aqua deion. | 1.0 | l |

Prior to inoculation the medium is filled into 16 ml test tubes and sterilized in an autoclave for 20 min at 121° C.

The tubes are incubated in an inclinated position at 28° C. on a rotary shaking machine with 220 rpm. Cultures with growth, observed as turbidity, in the presence of N-acetyl-1-phenylethylamine, but not in its absence, are further inoculated into 4 ml of sterile enrichment medium and also into control tubes without substrate (=second propagation).

Cultures of the fifth propagation were diluted $10^5$ and $10^6$ fold in sterile 69 mM potassium phosphate buffer, pH 7, and plated on solid medium consisting of the enrichment medium plus 20 g/l agar and on control plates without N-acetyl-1-phenylethylamine. Colonies morphologically different from those on the control plates are streaked—for cell isolation and determination of the enantioselectivity of the N-acetyl-1-phenylethylamine utilization—on selective agar plates containing enrichment medium plus 20 g/l agar, where the racemic N-acetyl-1-phenylethylamine is substituted by a) 3 g/l (S)-N-acetyl-1-phenylethylamine or b) (R)-N-acetyl-1-phenylethylamine. The plates are incubated for 3 to 10 days at 28° C. Strains growing only on one of the enantiomers of N-acetyl-1-phenylethylamine and appearing pure by colony morphology are cultured for 24–48 h at 28° C. on a shaker at 220 rpm in 25 ml medium (100 ml flasks) of the following composition (=basic medium with (R) or (S)-N-acetyl-1-phenylethylamine):

| | |
|---|---|
| Enantiomer of N-acetyl-1-phenylethylamine of the corresponding selective agar medium with growth | 3.0 g |
| Yeast extract | 2.0 g |
| Peptone | 2.0 g |
| Mineral salt solution ML1 | 1.0 l |
| pH-value | 7.0 |

0.5 ml of these precultures are used to inoculate the main cultures possessing the same medium and scale. After 24–48 h of incubation at 220 rpm and 28° C. the contents of the flasks is centrifuged (15 min. 9000×g) in a refrigerated Superspeed Centifuge (Dupont Co., Welmington, Del., USA), and the sedimented cells are suspended in 1 ml of 69 mM potassium phosphate buffer with pH 7. In Eppendorf vials 0.6 ml of these suspensions are mixed with 1.2 g of glass beads (diameter of 0.1–0.25 mm, Carl Roth GmbH, Karlsruhe, Germany) and are shaken for 10 min. in a glass bead mill (Retsch Co., Haan, Germany) at maximum velocity. After cooling the vials in an ice bath and centrifugation at 11500 rpm in a Biofuge 15 (Heraeus Sepatech, Osterode Germany) in order to remove the cell debris and the glass beads the supernatants (=crude cell extracts) are used as the enzyme source.

The assays for acylase activity are prepared in Eppendorf vials as follows:

| | |
|---|---|
| (S) or (R)-N-acetyl-1-phenylethylamine, 21 mM, in 69 mM potassium phosphate buffer, pH 7 | 380 μl |
| Crude extract | 20 μl |

After an incubation at 30° C. for a time period allowing the liberation of 0 to 3 mM of 1-phenylethylamine 400 μl of ice cooled acetone are added to stop the reaction. The tube is mixed vigorously, put on ice for about 15 min., and then is centrifuged for 4 min at 11500 rpm in a Biofuge 15 (Heraeus Sepatech, Osterode Germany). The supernatant is subjected to quantitative HPLC analysis. If activity assays contain crude extracts of cells grown in the presence of N-acetyl-1-phenylethylamine a control assay without substrate has to be prepared in parallel in order to determine the 1-phenylethylamine content of the crude extract. For HPLC analysis sample volumes of 20 μl are injected onto a RP-8 column (LiChroCART 125-4, LiChrospher 100 RP-8 (5 mm), guard column: LiChroCART 4-4, LiChrospher 100 RP-8 (5 mm), Merck Co., Darmstadt Germany). The following gradient with a flow rate of 1.25 ml/min. is applied for the separation of the substrate N-acetyl-1-phenylethylamine and the product 1-phenylethylamine:

Solvent A: potassium phosphate buffer, 3 mM, pH 3
Solvent B: 10% v/v of solvent A and 90% v/v of acetonitrile

| Time (min.) | Concentration of solvent A (v/v) | Concentration of solvent B (v/v) |
|---|---|---|
| 0 | 83 | 17 |
| 10 | 30 | 70 |
| 12 | 0 | 100 |
| 13 | 0 | 100 |
| 14 | 83 | 17 |
| 17 | 83 | 17 |

The substances in the eluate are detected by measuring the UV absorbance at 215 nm. The concentrations of the reaction product 1-phenylethylamine are calculated via the peak area using calibration curve from 0 to 5 mM.

One unit (U) of acylase activity is defined as the amount of enzyme catalyzing the liberation of 1 μmol of 1-phenylethylamine per minute. The acylase concentration in the samples is calculated according to the following formula:

U/ml [μmol/(ml×min)]=1-phenylethylamine concentration in the HPLC vial [mM]/(incubation time[min]×volume of the acylase containing sample [20 μl])×final assay volume [800 μl]×dilution factor (dilution of the acylase preparation before the test).

The specific activity is expressed as Units of acylase activity per mg of protein in the enzyme preparation determined by the BioRad Protein Assay (Biorad Co., Glattbrugg, Switzerland). The protein concentration of the sample is calculated by using a calibration curve with 0–1 mg/ml of bovine serum albumine. 26 bacterial strains were isolated possessing (S)-N-acetyl-1-phenylethylamine acylase activity. No strain was obtained containing an (R)-specific enzyme. Table 1 shows the specific activities of the 4 best organisms. *Rhodococcus equi* Ac6 (=DSM 10728) shows the highest specific activity in the crude extract and also the highest enzyme yield (45.2 U/l culture broth) and therefore, is selected as the producer of a (S)-1-phenylethylamine acylase. In the following the acylase of strain Ac6 is referred to as Ac6-acylase. In the examples given below the standard incubation time for shake flask cultures with strain Ac6 is 48 h.

TABLE 1

Production of (S)-N-acetyl-1-phenylethylamine acylase by the 4 favorite strains

| Strain | Specific activity (U/mg$_{protein}$*) | Enzyme yield (U/l$_{culture\ medium}$) |
|---|---|---|
| Ac6 | 0.41 | 45.2 |
| Ac18 | 0.28 | 36.1 |
| Ac12 | 0.36 | 28.3 |
| Ac25B | 0.066 | 13.6 |

*)U/mg$_{protein}$ in the crude cell extract

Example 2

Growth and Induction of the Acylase of *Rhodococcus equi* Ac6 a) Variation of the Inducer and Investigation of the Enantioselectivity of the Acylase Reaction

*R. equi* Ac6 is grown in basic medium containing 3 g/l (S)-N-acetyl-1-phenylethylamine or 3 g/l (R)-N-acetyl-1-phenylethylamine or no N-acetyl-1-phenylethylamine for 91 h by the shake flask culture technique described in example 1. By applying the methods given in example 1 the crude extracts are prepared and subjected to measurement of the protein concentration and the acylase activity using (S)-N-acetyl-1-phenylethylamine and (R)-N-acetyl-1-phenylethylamine as the substrates.

TABLE 2

Induction of *R. equi* Ac6 acylase

| Growth medium | OD$_{660}$ at cell harvest | Enzyme yield with (S)-amide[a] as the acylase substrate [U/l$_{culture\ broth}$] | Enzyme yield with (R)-amide[b] as the acylase substrate [U/l$_{culture\ broth}$] |
|---|---|---|---|
| BM | 0.46 | 0 | 0 |
| BM + (S)-amide | 1.52 | 38.2 | <0.4 |
| BM + (R)-amide | 0.19 | 0 | 0 |

BM: basic medium (see above), [a]: (S)-N-acetyl-1-phenylethylamine, [b]: (R)-N-acetyl-1-phenylethylamine The data given in table 2 show that (S)-N-acetyl-1-phenylethylamine has to be present in the growth medium to induce the acylase expression. (R)-N-acetyl-1-phenylethylamine is not effective as an inducer of the acylase of strain Ac6 and inhibits the growth of the bacterium. Furthermore, the acylase acts highly (S)-enantiospecific.

b) Variation of the Concentration of (S)-acetyl 1-phenylethylamine

*R. equi* Ac6 cells are inoculated into three 1 l Erlenmeyer flask containing each 100 ml of basic medium with 10 g/l yeast extract and 10 g/l meat extract as additional nutrients. The cells are grown (shake flask technique see example 1) until the OD$_{660}$ reaches about 2. Then the culture is split into eight portions of 25 ml and (S)-N-acetyl-1-phenylethylamine is added to the shake flasks in final concentrations of 0–7 g/l in steps of 1 g/l. The cells are further incubated for 25 h. Then the protein concentrations and acylase activities of the crude extracts are measured as described in example 1.

More than 2 g/l (S)-N-acetyl-1-phenylethylamine in the medium affect the acylase production negatively. (S)-N-acetyl-1-phenylethylamine inhibits the growth of the cells: the OD$_{660}$ decreases with increasing concentrations of (S)-N-acetyl-1-phenylethylamine in the medium.

In another experiment (S)-N-acetyl-1-phenylethylamine is added to the culture medium in final concentrations of 1 to 5 g/l in steps of 1 g/l directly after inoculation to one series of shake flasks (see example 1) and after 72 h of growth to another. Basic medium without peptone supplemented with 20 g/l meat extract and 20 g/l yeast extract is used. 96 h after inoculation the cells are harvested by centrifugation and the protein concentration and acylase activity in the crude extract are measured (see example 1).

3 g/l (S)-N-acetyl-1-phenylethylamine result in the maximal acylase yield (60 U/l$_{culture\ medium}$) if the inducer is added to the medium directly after inoculation, whereas 2 g/l (S)-N-acetyl-1-phenylethylamine lead to the maximal acylase production (20 U/l$_{culture\ medium}$) if the inducer is added 72 h after inoculation. By starting the cultivation in the presence of (S)-N-acetyl-1-phenylethylamine the acylase yield is three fold higher than in the culture where the inducer is added after 72 h of growth.

c) Variation of the Start pH-value

Shake flask cultures containing basic medium with 3 g/l (S)-N-acetyl-1-phenylethylamine varying in pH from 2.5 to 9.5 in steps of 0.5 pH units are grown for 65 h. Then the O.D.660 of the cultures as well as the protein concentrations and acylase activities of the crude extracts are measured (see example 1).

Optimum growth of *Rhodococcus equi* Ac6 and maximum acylase yield both are obtained between pH 5.5 and 7. The specific acylase activity, however, is rather constant over a broad range from pH 5.5 to pH 9.0.

d) Variation of the Nutrients

Shake flask cultures containing basic medium without peptone, with a lower yeast extract content of 0.5 g/l, 3 g/l racemic N-acetyl-1-phenylethylamine, and 2 g/l of an additional nutrient are incubated for 45 and 111 h, respectively. After determination of the O.D.660 the cells are harvested, disrupted, and the protein concentrations and acylase activities of the crude extracts are determined (see example 1).

TABLE 3

Growth and acylase production of *Rhodococcus equi* Ac6 with different nutrients

| | Additional nutrient | | | | | |
|---|---|---|---|---|---|---|
| | $OD_{660}$ at cell harvest | | Acylase yield $U/l_{[culture\ broth]}$ | | Specific activity $[mU/mg_{protein}]$ | |
| Time of cell harvest: | 45 h | 111 h | 45 h | 111 h | 45 h | 111 h |
| None | 0.76 | 0.58 | 24.0 | 17.8 | 0.41 | 0.44 |
| D-Glucose | 1.04 | 1.37 | 25.5 | 17.0 | 0.34 | 0.24 |
| D-Fructose | 0.89 | 1.02 | 19.4 | 11.6 | 0.28 | 0.20 |
| D-Lactose | 0.68 | 0.57 | 20.5 | 13.5 | 0.36 | 0.30 |
| D-Saccharose | 0.84 | 0.73 | 21.4 | 14.2 | 0.35 | 0.28 |
| Amylose | 0.83 | 0.76 | 24.0 | 19.0 | 0.34 | 0.27 |
| Glycerol | 0.73 | 0.84 | 22.4 | 14.7 | 0.36 | 0.29 |
| D-Mannitol | 0.69 | 0.54 | 20.9 | 15.7 | 0.36 | 0.30 |
| D-Sorbitol | 0.74 | 0.56 | 21.5 | 14.8 | 0.35 | 0.28 |
| Sodium acetate | 1.30 | 1.04 | 21.4 | 16.8 | 0.16 | 0.15 |
| Acetamide | 1.95 | 1.65 | 24.4 | 19.4 | 0.12 | 0.12 |
| L-Glutamate | 1.40 | 2.08 | 32.1 | 28.2 | 0.31 | 0.27 |
| Meat extract | 0.94 | 0.81 | 29.3 | 24.1 | 0.34 | 0.33 |
| Peptone from casein | 0.78 | 0.68 | 28.0 | 21.8 | 0.32 | 0.32 |
| Yeast extract | 1.13 | 1.14 | 34.2 | 28.6 | 0.33 | 0.31 |

The highest acylase yield after 45 h as well as after 111 h of incubation are achieved with yeast extract (see table 3). The expression of the acylase is positively influenced by the presence of L-glutamate and complex nutrients in the medium, which leads to higher acylase yields ($U/l_{medium}$), but not to increased specific activities. Cultures grown without additional nutrient show the highest specific acylase activity, but a low overall enzyme yield [$U/l_{culture\ broth}$] and a low cell density (O.D.660).

Example 3

Production of the Acylase of *Rhodococcus equi* Ac6 by Fermentation on 20 l Scale For the fermentation of *Rhodococcus equi* on 20 l scale a 30 l bioreactor is used equipped with an automatic regulation of the pH, the temperature, and the concentration of the dissolved oxygen ($PO_2$) and with an anti foam system. The fermentor is filled with 20 l of basic medium containing 3 g/l of racemic N-acetyl-1-phenylethylamine and 5 g/l of yeast extract. After autoclavation of the medium for 30 min. at 121° C. and cooling down to 28° C. the bioreactor is inoculated to an initial O.D.660 of 0.05 with 1 l of shake flask culture, which has been grown before in 5 portions of 200 ml in 1 l Erlenmeyer flasks during 84 h at 28° C. and 220 rpm. The conditions during the fermentation are:

| Temperature | 28 | ° C. |
|---|---|---|
| pH-value | 6.5 | adjusted with 2 N HCl |
| Aeration | 8 | l/min = 0.375 VVM |
| $pO_2$ | 50 | % of saturation, regulated via agitator speed |
| Maximum agitator speed | 750 | rpm |
| Antifoam agent | | SAG 471 |

Samples of 25 ml culture medium are taken at different time points. The O.D.660 values of the culture broth as well as the protein contents and the acylase activities of the crude extracts are measured (see example 1).

The maximum enzyme yield ($U/l_{culture\ medium}$) is reached after 30 h of incubation and remains constant at least during the next 18 h. After 48 h of cultivation the fermentation broth is cooled down to 15° C. By continuous flow centrifugation using a Sorvall TZ-28 rotor in a refrigerated Sorvall RC5B Superspeed Centrifuge (Dupont Co., Wilmington, Del., USA) 41 g of cells (wet weight) are harvested containing 680 U of Ac6-acylase with a specific activity of 0.19 U/mg protein in the crude extract. The cells are resuspended in 103 ml of 69 mM potassium phosphate buffer, pH 7, and stored at −20° C.

Example 4

Purification of the Acylase of *Rhodococcus equi* Ac6 a) Preparation of the Crude Extract in Preparative Scale 100 ml of cell suspension prepared as described in example 3 are thawn and poured into a 600 ml glass beaker containing 150 ml of glass beads (diameter of 0.1–0.25 mm). The beaker is cooled in an ice bath during the cell disruption with a Philips HR1385 professional handblender, which is operated 6–8 times for 2 min. interrupted by breaks for 5 min. After sedimentation of the glass beads the supernatant is removed and 150 ml of 69 mM potassium phosphate buffer pH 7.0 are added to the glass beads. By short mixing and settling of the glass beads a second supernatant is obtained. The two supernatants are combined and centrifuged (20 min., 9000 rpm) in a Sorvall RC5B refrigerated Superspeed Centrifuge using a Sorvall GS-3 aluminum rotor. The supernatant of the centrifugation is used as the crude cell extract for the purification of the acylase. The crude extract can be stored at −20° C. for at least two month without loss of activity, and intermediate thawing and freezing only results in a loss of activity of 5%.

b) Ammonium Sulfate Precipitation

To 100 ml of ice cooled crude extract (preparation see example 4a) crystalline ammonium sulfate is added slowly to a final concentration of 25% saturation. After the ammonium sulfate is dissolved under gentle stirring, the solution is kept on ice for about 30 min. and then the precipitated protein is sedimented by centrifugation for 60 min. at 9000 rpm in a Du Pont RC5B refrigerated Superspeed Centrifuge using a Sorvall GS-3 aluminum rotor. Further ammonium sulfate was added to the supernatant to a final concentration of 85% and a second protein precipitation is performed as described above. The precipitated protein comprising the Ac6-acylase is dissolved in 150 ml of an ammonium sulfate solution (concentration 30% saturation) in 69 mM potassium phosphate buffer, pH 7.

c) Hydrophobic Interaction Chromatography (HIC) on Butyl-Fractogel

For HIC a Merck Fraktogel TSK Butyl-650(S) column (26×310 mm) is equilibrated with a 30% saturated ($NH_4$)

₂SO₄ solution (in phosphate buffer, 69 mM, pH 7.0). After loading the column with 75 ml of the final protein solution obtained after the ammonium sulfate precipitation in example 4b) the column is washed with a 30% saturated ammonium sulfate solution (in phosphate buffer, 69 mM, pH 7.0) until the UV detector signal reaches the baseline level again. Then a gradient decreasing from 30% to 0% ammonium sulfate with a total volume of 825 ml and a flow rate of 1.8 ml/min. is applied to the column. The fraction size is 12 ml. The Ac6-acylase activity of the fractions is measured (see example 1).

The Ac6-acylase elutes from the column between 8 to 4% saturation of ammonium sulfate. The 5 most active fractions are pooled and desalted by diafiltration and concentrated to a final volume of 23 ml in a CEC column concentrator equipped with an YM 30000 membrane (Amicon Inc., Beverly, Mass., USA). The diafiltration is achieved by repeatedly adding potassium phosphate buffer, 69 mM, pH 7, to the concentrated protein solution and ensuing a reconcentration step.

Table 4 summarizes the results of the purification. The Ac6-acylase preparation obtained by only one chromatographic step appears homogenous by SDS polyacrylamide gel electrophoresis performed with a Phast System using gradient Phast Gels of the type 10–15 (containing 10–15% polyacrylamide) (Pharmacia Co., Dübendorf, Switzerland) and coomassie blue staining. For the electrophoresis and the staining procedure the standard methods given by Pharmacia for Phast Gel gradient media are used (Pharmacia Phast System separation technique file no. 110: "SDS-PAGE", and file no. 200: "Fast Coomassie Blue Staining", Pharmacia, Uppsala, Sweden).

TABLE 4

Purification of the Ac6-acylase

| Purification step | Total Acylase (U) | Recovery (%) | Specific activity (U/mg protein) | Enrichment factor |
|---|---|---|---|---|
| Cell breakage | 502 | 100 | 0.19 | 1.0 |
| Ammonium sulfate precipitation | 374 | 74 | 0.21 | 1.1 |
| HIC + UF-diafiltration/ concentration | 267 | 53 | 0.76 | 4.0 |

HIC: Hydrophobic Interaction Chromatography, UF: Ultrafiltration

If a crude extract of a lesser specific activity is used, it is necessary to subject the acylase further chromatographic purification steps to obtain a homogenous enzyme preparation, e.g. by amino exchange chromatography on Mono-Q or gel filtration on Superose 12 HR (Pharmacia, Uppsala, Sweden) described in example 5.

Example 5

Determination of the Molecular Weight and the Subunit Structure of the Ac6-acylase A Pharmacia Superose 12HR 10/30 gel filtration column (10×300 mm) is used to determine the molecular weight of the native Ac6-acylase. The elution is performed using 69 mM potassium phosphate buffer, pH 7.0, supplemented with NaCl 100 mM, with a flow rate of 0.3 ml/min. 50 μl of the purified and concentrated Ac6-acylase obtained in example 4c are applied to the column. The molecular weight of the native enzyme is determined using a calibration curve representing the $K_{AV}$-values of the calibration proteins (see table 5) against the logarithm of the molecular weight. The $K_{AV}$ value is defined as follows:

$$K_{AV}=(V_{elution}-V_0)/(V_{column}-V_0)$$

$V_0$=void volume=$V_{elution}$ of dextran blue=7.65 ml, $V_{column}$=column volume=23.6 ml.

A molecular weight of 94000±3000 ($K_{AV}$=0.33±0.04) is measured for the native Ac6-acylase.

TABLE 5

Calibration proteins for the determination of the molecular weight of the native Ac6-acylase by gel filtration

| Protein | $V_{elution}$ [ml] | $K_{AV}$ | Molecular weight |
|---|---|---|---|
| Dextran blue from Leuconostoc spp.*) | 7.65 | 0 | ~2000000 |
| Myoglobin from horse heart | 14.8 | 0.451 | 17800 |
| Trypsin inhibitor from soy beans | 14.7 | 0.440 | 20100 |
| Peroxidase from horse radish | 13.6 | 0.371 | 40000 |
| Bovine serum albumin | 12.9 | 0.330 | 67000 |
| Lactate dehydrogenase from bovine heart | 12.2 | 0.285 | 140000 |
| Aldolase from rabbit muscle | 12.1 | 0.281 | 161000 |

*)used for the determination of $V_0$

In order to determine the subunit structure SDS-polyacrylamide gelelectrophoresis is applied as described in example 4c. The molecular weight of the denatured acylase is determined using a calibration curve showing the migration distances against the logarithm of the molecular weights of the marker proteins of a Pharmacia Low Molecular Weight Calibration Kit.

The denatured Ac6-acylase has a molecular weight of 50000±2000. This result in comparison with the molecular weight determined for the native enzyme indicates a homodimeric substructure for the Ac6-acylase.

Example 6

Determination of the Isoelectric Point (IEP)

Isoelectric focusing (IEF) is done on gels of the type Pharmacia Phast Gel IEF 3–9 (forming a gradient from pH 3 to pH 9) using the Pharmacia Phast System. The IEP of the enzyme is determined in comparison with the proteins of the Pharmacia Low pI Calibration Kit (pH 2.5–pH 6.5). For the isoelectric focusing and the staining procedure the standard methods given by Pharmacia for Phast Gel IEF media are used (Pharmacia Phast System separation technique file no. 100: "IEF and titration curve analysis", and file no. 200: "Fast Coomassie Blue staining", Pharmacia, Uppsala, Sweden). The IEP of the Ac6-acylase is around pH 3.5.

Example 7

Dependence of the Reaction Velocity of the Ac6-acylase on the pH Value

Enzyme tests as described in example 1 are performed in buffers ranging in pH from 5.71 to 9.88 (pH 5.71, 6.09, 6.58, 7.0, 7.47: potassium phosphate buffer, 69 mM; pH 7.48, 8.0, 8.4, 8.82, 9.10: Tris-HCl buffer, 100 mM; pH 9.38, 9.88: glycine-NaOH buffer, 100 mM). The incubation time is 30 min. using the final acylase preparation obtained in example 4c diluted 20 times as the enzyme source.

The Ac6-acylase shows a broad activity optimum between pH 6.0 and pH 8.5 with a maximum between pH 6.5 and pH 7.0.

Example 8

Influences of Activators and Inhibitors on the Ac6-acylase Activity

In the presence of various potential enzyme activators and inhibitors activity assays are performed according to the scheme given in example 1 by applying the following conditions and final concentrations:

| | |
|---|---|
| Tris-HCl, pH 8 | 100 mM |
| (S)-N-acetyl-1-phenylethylamine | 20 mM |
| Purified acylase from example 4 c | 0.02 U/ml |
| Incubation time | 120 min. |

TABLE 6

Activity of the Ac6-acylase in the presence of potential enzyme activators and inhibitors

| Compound | Relative activity (%) | |
|---|---|---|
| None | 100 | |
| | 1 mM | 10 mM |
| Metal cations: | | |
| $VCl_3$ | 89 | (94) |
| $CoCl_2$ | 69 | (83) |
| $MnCl_2$ | 87 | (87) |
| $ZnCl_2$ | 68 | (47) |
| $MgCl_2$ | 90 | 99 |
| $NiCl_2$ | 40 | 10 |
| $CaCl_2$ | 90 | (83) |
| $CuCl_2$ | 88 | 41 |
| $PbCl_2$ | 95 | (99) |
| $BaCl_2$ | 95 | (99) |
| $CdCl_2$ | 85 | (38) |
| $FeCl_3$ | 101 | (92) |
| Chelating agents: | | |
| EDTA | 102 | 104 |
| Citrate | 106 | 91 |
| Thiol reducing agents: | | |
| Dithiothreitol | 103 | 100 |
| Mercaptoethanol | 104 | 108 |
| Glutathion, reduced | 106 | 102 |
| Thiol group blocking agents: | | |
| Iodoacetamide | 87 | 32 |
| Protease inhibitor: | | |
| Phenylmethyl-sulfonyl fluoride | 0 | 0 |
| | 0.01 mM: 17 | 0.1 mM: 4.8 |

Relative activities given in brackets indicate formation of precipitates during the enzyme assays.

None of the tested metal cations except $Ni^{2+}$ and to some extent $Zn^{2+}$ in 1 mM concentration affect the acylase activity much (see table 6). In 10 mM concentration $Zn^{2+}$, $Ni^{2+}$, $Cu^{2+}$ and $Cd^{2+}$ show considerable inhibition of the acylase.

Chelating agents and thiol reducing agents do not affect the acylase activity, whereas 10 mM iodoacetamide and phenylmethylsulfonyl fluoride already in a concentration of 0.01 mM are strongly inhibitory. The strong inhibition by phenylmethylsulfonyl fluoride suggests a serine protease reaction mechanism for the Ac6-acylase.

Example 9

Temperature Stability of the Ac6-acylase

Samples of the final acylase preparation obtained in example 4c are diluted 45 fold with 69 mM potassium phosphate buffer, pH 7, and incubated for various time periods at different temperatures. After the temperature treatment standard activity assays (see example 1) are carried out at 30° C.

TABLE 6

Temperature stability of the Ac6-acylase

| | Residual activity (%) | | | |
|---|---|---|---|---|
| Time (min.) | 30° C. | 37° C. | 39.5° C. | 44° C. |
| 15 | 98 | 92 | 85 | 23 |
| 30 | 96 | 90 | 77 | 11 |
| 60 | 96 | 88 | 62 | 7.0 |
| 120 | 94 | 83 | 45 | 6.3 |
| 240 | 94 | 84 | 28 | 4.7 |

As it can be seen in table 6 the acylase retains almost all of its initial activity after 4 h of incubation at 30 and 37° C., whereas at 39.5 and 44° C. the enzyme is deactivated considerably.

At 30° C. even after 34 days still 94% of the initial acylase activity are present.

Example 10

Dependence of the Reaction Velocity of the Ac6-acylase on the Concentration of (S)-N-acetyl-1-phenylethylamine Activity assay under the standard conditions given in example 1 with an incubation time of 10 min. are performed using different initial concentrations of (S)-N-acetyl-1-phenylethylamine and the final Ac6-acylase preparation obtained in example 4c, which has been diluted 5 fold with 69 mM potassium phosphate buffer, pH 7, as the enzyme source. The Michaelis constant $K_m$ is calculated from the substrate concentrations and the corresponding reaction velocities by numerical nonlinear regression with the program "SigmaPlot for Windows" (Jandel Scientific GmbH, Schimmelbusch, Germany) to the formula: $v=V_m \times S/(S+K_m)$. v: reaction velocity (U/ml=mM/min.), $V_m$: maximum reaction velocity (U/ml), S=(S)-N-acetyl-1-phenylethylamine concentration (mM).

The $K_m$ value for (S)-N-acetyl-1-phenylethylamine is 0.6 mM±0.1 mM.

Example 11

Isolation of Microorganisms with (R)-1-phenylethylamine Acylase Activity

In general the procedure given in example 1 is applied with the following modifications:

43 soil and water samples are investigated.

The liquid medium for the enrichment cultures and the selective agar plates, on which the diluted enrichment cultures are plated to obtain single colonies, contains 3 g/l (R)-N-acetyl-1-phenylethylamine instead of racemic N-acetyl-1-phenylethylamine and in addition 2 ml/l of the following vitamin solution:

| | |
|---|---|
| Biotin | 5 mg |
| Nicotinic acid | 500 mg |
| 4-Aminobenzoate | 50 mg |
| Calcium pantothenate | 500 mg |
| Thiamine * HCl | 500 mg |
| Vitamin $B_{12}$ | 0.5 mg |
| Pyridoxamine | 500 mg |
| Pyridoxine * HCl | 500 mg |
| Riboflavin | 250 mg |
| Folic acid | 15 mg |
| Nicotinamide | 250 mg |
| Aqua deion. | 1 l |

The liquid medium for the first propagation is supplemented with 0.5 g/l, for the second propagation with 0.2 g/l of sodium acetate in order to facilitate the growth of acetic acid consuming microorganisms in the beginning of the enrichment.

Only 3 propagations of enrichment culture are performed. The basic medium to grow the cells for the activity tests only contains 1 g/l of yeast extract and peptone.

(R)-N-acetyl-1-phenylethylamine is used as the substrate for the activity assays with the AcR5b-acylase.

Only 3 strains with a (R)-specific acylase activity could be isolated (see table 7). *Arthrobacter aurescens* AcR5b (=DSM 10280) shows the highest specific activity and is selected as the producer of the (R)-N-1-phenylethylamine acylase, which is in the following referred to as AcR5b-acylase. In the examples given below the standard incubation time for shake flask cultures with strain AcR5b is 23 h.

Table 7: Production of (R)-N-acetyl-1-phenylethylamine acylase activity by the three (R)-specific strains 11 in steps of 0.5 pH units are grown for 23 h. Then the $OD_{660}$ of the cultures as well as the protein concentrations and acylase activities of the crude extracts are measured (see example 11).

Optimum growth of *Arthrobacter aurescens* AcR5b and maximum acylase yield (U/l culture broth) are both obtained between pH 5.5 and 9. No growth occurs below pH 4.5 and pH 10. For further cultivation of strain AcR5b pH 7 is chosen.

c) Variation of the Temperature

Shake flask cultures including the measurement of the O.D.660, the acylase activity, and the protein content of the crude extracts are performed with strain AcR5b according to example 11 by varying the temperature between 22–36° C. in steps of 2° C. The basic medium without (R)-N-acetyl-1-phenylethylamine is used. Strain AcR5b grows most rapidly between 28 and 32° C. No growth occurs at 36° C. At 28° C. the maximum enzyme yield $(U/l_{culture\ broth})$ is obtained.

d) Variation of the Nutrients

In shake flask cultures with strain AcR5b the basic medium without (R)-N-acetyl-1-phenylethylamine is supplemented with different nutrients at a concentration of 5 g/l, respectively. The O.D.660, the acylase-activity, and the protein content of the crude extracts are determined as described in example 11.

Among the best results regarding the total enzyme yield (U/l culture broth) are those obtained with sorbitol and meat extract, which are chosen for the further cultivation of strain AcR5b.

| Strain | Incubation time (days) | O.D. 660 | Acylase yield with (S)-amide as the enzyme substrate $(U/l_{culture\ broth})$ | Acylase yield with (R)-amide as the enzyme substrate $(U/l_{culture\ broth})$ | Specific activity with (R)-amide (U/$mg_{protein\ in\ the\ crude\ extract}$) |
|---|---|---|---|---|---|
| AcR5b | 1 | 3.08 | 0.0 | 137 | 0.98 |
| AcR11a | 2 | 4.16 | 0.0 | 152 | 0.84 |
| AcR30a | 4 | 2.39 | 4.8 | 24 | 0.17 |

(S) and (R)-amide: (S) and (R)-N-acetyl-1-phenylethylamine

Example 12

Growth and Induction of the Acylase of *Arthrobacter aurescens* AcR5b a) Variation of the Concentration of (R)-acetyl 1-phenylethylamine

*Arthrobacter aurescens* AcR5b was cultured in shake flasks (see example 11) using the basic medium, in which the concentration of (R)-N-acetyl-1-phenylethylamine was varied between 0.5 to 4 g/l in steps of 0.5 g/l. The O.D.660, the acylase-activity, and the protein content of the crude extracts are measured as described in example 11.

The maximum amount of AcR5b-acylase is produced in the medium without (R)-N-acetyl-1-phenylethylamine. Therefore, the enzyme is expressed constitutively. Furthermore, the specific activity of the acylase decreases with increasing concentrations of (R)-N-acetyl-1-phenylethylamine in the culture broth.

b) Variation of the Start pH-value

Shake flask cultures containing basic medium without (R)-N-acetyl-1-phenylethylamine varying in pH from 3.5 to

TABLE 8

Growth and acylase production of *Arthrobacter aurescens* AcR5b with different nutrients

| Additional nutrient | O.D. 660 | Acylase yield $[U/l_{culture\ broth}]$ | Specific activity $[U/mg_{protein}]$ |
|---|---|---|---|
| None | 1.50 | 134 | 1.12 |
| Carbon sources: | | | |
| D-Fructose | 3.97 | 169 | 1.11 |
| D-Galactose | 4.64 | 173 | 1.19 |
| D-Glucose | 4.82 | 176 | 0.96 |
| D-Maltose Monohydrate | 5.18 | 157 | 1.06 |
| Malt extract | 4.63 | 189 | 0.87 |
| Saccharose | 6.08 | 156 | 0.75 |
| Starch (soluble) | 1.64 | 161 | 1.11 |
| Glycerol | 7.08 | 182 | 0.79 |
| D-Mannitol | 6.05 | 174 | 0.89 |
| D-Sorbitol | 5.9 | 217 | 1.00 |
| Sodium acetate | 2.68 | 180 | 0.70 |
| Tri-sodium citrate dihydrate | 2.77 | 153 | 0.66 |

TABLE 8-continued

Growth and acylase production of *Arthrobacter aurescens* AcR5b with different nutrients

| Additional nutrient | O.D. 660 | Acylase yield [U/l$_{culture\ broth}$] | Specific activity [U/mg$_{protein}$] |
|---|---|---|---|
| Nitrogen sources: | | | |
| AC-Broth (Difco) | 4.23 | 190 | 1.17 |
| Bacto-Soytone | 4.31 | 190 | 0.86 |
| Casamino acids | 3.75 | 160 | 1.32 |
| Casein hydrolysate | 3.53 | 199 | 1.21 |
| Casitone | 4.75 | 210 | 1.05 |
| **Corn Steep Liquor* | 4.48 | 197 | 1.45 |
| Fish protein hydrolysate* | 4.20 | 93 | 0.52 |
| L-Glutamic acid | 4.88 | 203 | 1.04 |
| L-Glutamine | 4.49 | 159 | 1.11 |
| Meat extract | 3.38 | 212 | 0.87 |
| Peptone from casein | 4.63 | 211 | 1.05 |
| Peptone from soybeans | 3.95 | 175 | 1.07 |
| Peptone C (technical grade) | 2.75 | 136 | 1.32 |
| Soybean powder full fat* | 1.02 | 6.5 | 0.09 |
| Yeast extract (Difco) | 3.94 | 157 | 0.63 |
| Yeast extract, technical grade | 3.86 | 168 | 1.01 |

*not completely dissolved,
**formation of cell aggregates e) Variation of the Concentration Ratio Between the Carbon and Nitrogen Source In shake flask cultures with strain AcR5b the mineral solution ML1 without ammonium sulfate is supplemented with sorbitol and meat extract at different ratios, but the total concentration of both nutrients was held constant at 7 g/l. The O.D.660, the acylase-activity, and the protein content of the crude extracts are determined as described in example 11.

The optimum yield of the AcR5b-acylase (375 U/l culture broth) was obtained at a ratio of sorbitol to meat extract of 4:3.

f) Variation of the Total Nutrient Concentration

The mineral solution ML1 without ammonium sulfate is supplemented with sorbitol and a complex nitrogen source in the concentration ratio of 4:3 by varying the total concentration of both nutrients (7, 14, 21, 28, and 42 g/l). Meat extract, peptone from casein, and yeast extract of technical grade are used as the complex nitrogen sources. The shake flask culture (see example 11) is performed in 1 l Erlenmeyer flasks filled with 200 ml of medium, which have been inoculated with 3 ml of a preculture. After 11, 20, 27, 35, 46.5, and 70 h of incubation samples of 25 ml are removed from the flasks and the O.D.660, the acylase activity, and the protein content of the crude extracts are measured.

The maximum AcR5b-acylase yield was obtained with peptone (table 8) after 70 h of incubation.

Table 9: Growth and acylase production by *Arthrobacter aurescens* AcR5b with different complex nitrogen sources after 70 h of incubation at the total nutrient concentration resulting in the maximum enzyme yield.

| Nitrogen source | Total nutrient concentration (g/l) | O.D. 660 | Acylase yield (U/l$_{culture\ broth}$) | Specific activity (U/mg$_{protein}$) |
|---|---|---|---|---|
| Peptone from casein | 28 | 16.0 | 1470 | 4.5 |
| Meat extract | 21 | 9.7 | 1070 | 4.2 |
| Yeast extract | 21 | 8.2 | 950 | 3.5 |

Example 13

Production of the Acylase of *Arthrobacter aurescens* AcR5b by Fermentation on 20 l Scale The fermentative production of the AcR5b-acylase on 20 l scale is performed as described in example 3 with the following modifications:

The composition of the culture medium is peptone from casein 12 g/l, sorbitol 16 g/l, antifoam agent SAG 471 ml/l, dissolved in mineral salt solution ML1 (example 1) without ammonium sulfate, pH 7.

The agitator speed is adjusted to 500–800 rpm, the set point for the dissolved oxygen concentration to 40% saturation, and the airflow rate to 15 l/min (=0.75 VVM).

The bioreactor is inoculated with 0.5 l of preculture grown in portions of 2 times 250 ml in 1 l Erlenmeyer flasks at 28° C. and 220 rpm for 19 h.

The cells are harvested by continuous centrifugation after 33 h of cultivation.

The specific activity and also the total acylase yield still increase significantly in the stationary growth phase up to 5.26 U/mg$_{protein}$ and 6420 U/l$_{culture\ broth}$, respectively, at an O.D.660 value of 25. The wet cell mass is resuspended in 69 mM potassium phosphate buffer, pH 7, to a final concentration of 40% weight per volume.

Example 14

Purification of the Acylase of *Arthrobacter aurescens* AcR5b a) Preparation of the Crude Cell Extract on Preparative Scale 100 ml of the thawn cell suspension obtained in example 13 are cooled in an ice bath and sonicated with a Sonicator W-385 (Heat System Ultrasonics, Farmingdale, USA) using the ½" standard horn under the following conditions: Cycle time 1 sec., duty cycle 50%, output control 8, and sonicating time 25 min. After removing the cell debris by centrifugation in a refrigerated centrifuge at 13400 g for 20 min. the supernatant is used as the crude cell extract for the further purification.

b) Precipitation of Nucleic Acids with Polyethylene Imine

The crude extract obtained in example 14a) is mixed with a 10% (weight/volume) solution of polyethylene imine with a molecular weight of 30000–40000, pH 7, to a final concentration of the polymer of 0.3%. The solution is stirred for 30 min. at 0° C. and the precipitate is removed by centrifugation at 27000 g and 4° C. for 30 min.

c) Ammonium Sulfate Precipitation

To the supernatant from example 14b) solid ammonium sulfate is added a final concentration of 30% saturation. The mixture is gently stirred at 0° C. and then centrifuged at 4° C. and 27000 g for 30 min. To the supernatant further ammonium sulfate is added to a final concentration of 70% saturation. The precipitated protein containing the acylase is sedimented by centrifugation (see above) and dissolved in 40 ml of 69 mM potassium phosphate buffer, pH 7.

d) HIC on Butyl-Fractogel 5.76 g of ammonium sulfate are dissolved in the final protein solution from example 14c) to reach a final concentration of 25% saturation. The HIC is performed according to example 4c) with the only exceptions, that the column is preequilibrated with a 25% ammonium sulfate solution and the gradient is run from 25 to 0% saturation of ammonium sulfate.

After washing the non bound protein from the column with a 25% ammonium sulfate solution the AcR5b-acylase elutes between 13 and 10% of ammonium sulfate. The enzyme represents the only protein peak of the whole chromatogram. The active fractions are pooled, desalted, and concentrated as described is example 4c).

e) Anion Exchange Chromatography on Macro Prep High-Q

A 16×125 mm column filled with Macro Prep High-Q support (Biorad, Glattbrugg, Switzerland) is equilibrated with 250 ml of 69 mM potassium phosphate buffer pH 7. After half of the concentrated protein solution obtained in example 14d) is loaded onto the gel a gradient from 0 to 1 M of NaCl in 70 mM potassium phosphate buffer, pH 7, with a volume of 125 ml is applied to the column. The flow rate is 1 ml/min., the fraction size 1.5 ml. The protein concentration in the eluate is monitored via a UV detector signal and the acylase activity and the protein content of the active fractions are measured as described in example 11.

The acylase activity elutes between 0.4 and 0.6 M NaCl. The activity peak is identical with the only UV detector peak of the chromatogram. The active fractions are pooled and concentrated by ultrafiltration (see example 4c) to a final protein concentration of 2 mg/ml.

Table 10 summarizes the purification of the AcR5b-acylase. The AcR5b-acylase fractions obtained by anion exchange chromatography all show two bands by SDS polyacrylamide gel electrophoresis (SDS-PAGE, see example 4c) and appear homogenous by native PAGE, which is also performed with a Phast System using gradient Phast Gels of the type 8–25 (containing 8–25% polyacrylamide) (Pharmacia Co., Dübendorf, Switzerland). The gels are stained with coomassie blue (see example 4c). For the native PAGE the standard method given by Pharmacia for Phast Gel gradient media is used (Pharmacia Phast System separation technique file no. 120: "Native PAGE".

TABLE 10

Purification of the AcR5b-acylase

| Purification step | Total acylase (U) | Recovery (%) | Specific activity (U/mg) | Enrichment factor |
|---|---|---|---|---|
| Cell breakage | 5593 | 100 | 1.9 | 1.0 |
| Polyethylene imine precipitation | 5262 | 94 | 3.0 | 1.6 |
| ammonium sulfate precipitation | 4408 | 79 | 2.8 | 1.5 |
| HIC + UF-diafiltration/ concentration | 4186 | 75 | 8.2 | 4.3 |
| Anion exchange chromatography | 3725 | 67 | 10.0 | 5.2 |

Example 15

Determination of the Molecular Weight and the Subunit Structure

The molecular weight of the native AcR5b-acylase is 220000±10000 measured by gel chromatography according to example 5. In the SDS-PAGE (see example 5) the denatured acylase of *Arthrobacter aurescens* AcR5b shows two bands corresponding to a molecular weight of 89000±3000 and 16000±1000. These results indicate that the AcR5b-acylase is a tetramer consisting of 2 identical large and two identical small subunits (subunit structure of the type $\alpha_2\beta_2$).

Example 16

Dependence of the Reaction Velocity of the AcR5b-acylase on the pH Value

Enzyme tests as described in example 1 with (R)-N-acetyl-1-phenylethylamine are performed in buffers ranging in pH from 5.5 to 11.0 (pH 5.5, 6.0, 6.5, 7.0, 7.5, 8.0: potassium phosphate buffer, 69 mM; pH 7.5, 8.0, 8.5, 9.0: Tris-HCl buffer, 100 mM; pH 8.5, 9.0, 9.5, 10.0, 10.5, 11.0: glycine-NaOH buffer, 100 mM). The incubation time is 3 min. using the final acylase preparation obtained in example 4d as the enzyme source.

The acylase activity shows a broad pH optimum between pH 7.5 and 9 with a maximum at pH 8.

Example 17

Influence of Activators and Inhibitors on the AcR5b-acylase Activity

40 μl of the concentrated enzyme solution from example 4d) are mixed with 360 μl of 1 and 10 mM solutions of the potential activators/inhibitors in 100 mM Tris-HCl buffer, pH 8, and incubated at room temperature for 30 min. These preincubated acylase solutions are used as the enzyme source for activity assays in the presence of the activator/ inhibitor (see example 8) in the concentration used for the preincubation. The incubation time is 12 min. For the EDTA reactivation the acylase is first preincubated with the metal cation at 1 mM concentration (see above). After adding EDTA to a final concentration of 10 mM in form of a 110 mM solution in 100 mM Tris-HCl, pH 8, the acylase is preincubated a second time for 30 min., before the standard activity assay is performed.

6 of the bivalent metal cations inhibit the enzyme remarkably, but in all cases the activity can at least partially be restored with EDTA. EDTA alone and FeCl$_3$ enhance the acylase activity. Dithiothreitol, iodoacetamide, and phenymethylsulfonyl fluoride inhibit the enzyme at a low to moderate degree.

TABLE 11

Activity of the AcR5b-acylase in the presence of potential enzyme activators and inhibitors

| Compound | Relative activity (%) | | |
|---|---|---|---|
| None | 100 | | |
| | 1 mM | 10 mM | EDTA reactivation |
| Bivalent metal cations: | | | |
| CoCl$_2$ | 26 | (15) | 91 |
| MnCl$_2$ | 99 | (60) | n.d. |
| ZnCl$_2$ | <1.5 | (0) | 75 |
| MgCl$_2$ | 103 | 93 | n.d. |
| NiCl$_2$ | 14 | 0 | 85 |
| CaCl$_2$ | 92 | 88 | n.d. |
| CuCl$_2$ | 50 | 0 | 86 |
| PbCl$_2$ | 79 | 9 | 102 |
| BaCl$_2$ | 92 | 89 | n.d. |
| CdCl$_2$ | 5 | 0 | 79 |
| FeCl$_3$ | 121 | 132 | n.d. |
| VCl$_3$ | 96 | (106) | n.d. |
| Chelating agents: | | | |
| EDTA | 119 | 121 | n.d. |
| Citrate | 122 | 100 | n.d. |
| Thiol reducing agents: | | | |
| Dithiothreitol | 35 | 5.4 | n.d. |
| Mercaptoethanol | 115 | 69 | n.d. |
| Glutathion, reduced | 113 | 112 | n.d. |
| Thiol group blocking agents: | | | |
| Iodoacetamide | 96 | 29 | n.d. |

TABLE 11-continued

Activity of the AcR5b-acylase in the presence of potential enzyme activators and inhibitors

| Compound | Relative activity (%) | | |
|---|---|---|---|
| Protease inhibitor: | | | |
| Phenylmethyl-sulfonyl fluoride | 44 | n.d. | n.d. |

Relative activities in brackets indicate formation of precipitates in course of the enzyme assays. n.d.: not determined.

Example 18

Stability of the AcR5b-acylase a) Temperature Stability

Samples of the final acylase preparation obtained in example 14d are diluted 10 fold with 69 mM potassium phosphate buffer, pH 7, and incubated for 30 min. at different temperatures. A sample incubated on ice serves as the 100% standard. Afterwards the remaining acylase activities of the samples are measured via the standard activity assays (see example 11).

Between 21 and 30° C. no loss of acylase activity is observed (see table 12). Whereas at 50° C. still 60% of the initial activity are retained after 30 min. of incubation, at 56° C. the enzyme is completely deactivated.

TABLE 12

Residual activity of the AcR5b-acylase after incubation at different temperatures for 30 min.

| Temperature (° C.): | 0 | 21 | 25 | 30 | 35 | 40 | 45 | 50 | 56 | 60 |
|---|---|---|---|---|---|---|---|---|---|---|
| Residual activity (%): | 100 | 95 | 102 | 100 | 89 | 82 | 68 | 60 | 0 | 0 |

When the diluted acylase (see above) is incubated at 0–4° C. for 16 and for 135 days, the relative residual activities are still 100 and 95% of the initial value. After an incubation at 23° and 30° C. for 16 days, 86 and 65% of the initial activity are retained.

b) pH-Stability

The final enzyme preparation from example 4d) is diluted 20 fold with the buffers given in example 16 and incubated at room temperature (about 23° C.) for one week. Then the remaining activity of the samples is measured as described in example 11. 100% activity correspond to the value obtained immediately after the dilution with the pH 7 buffer.

The enzyme is rather stable between pH 7 and 9 (100% residual activity), but beyond these limits the stability declines sharply.

c) Stability During Freezing

The final acylase preparation obtained in example 14d) is diluted 20 fold with 69 mM potassium phosphate buffer (pH 7), with and without cryoprotective agents (see table 13). The enzyme solutions are frozen at −20 and −80° C. After 2.5 h and 9 days the samples are thawn and the residual acylase activity is measured as described in example 11.

The data given in table 13 demonstrate that the acylase is deactivated by storage in the frozen state. The stability can remarkably be enhanced by addition of cryoprotective agents.

TABLE 13

Influence of freezing on the AcR5b-acylase activity

| | Relative activity (%) | | | |
|---|---|---|---|---|
| Cryoprotective agent | 2.5 h, −20° C. | 9 days, −20° C. | 2.5 h, −80° C. | 9 days, −80° C. |
| None | 67 | 0 | 100 | 34 |
| 5% Glycerol | 100 | 89 | 100 | 97 |
| 50% Glycerol | 77 | 98 | 100 | 90 |
| 10% $(NH_4)_2SO_4$ | 100 | 81 | 92 | 83 |
| 10% Saccharose | 100 | 100 | 100 | 92 |

Example 19

Dependence of the Reaction Velocity of the AcR5b-acylase on the Concentration of the Substrate Activity assays are performed under the standard conditions given in example 11 with an incubation time of 30 min. using different initial concentrations of (R)-N-acetyl-1-phenylethylamine and racemic N-acetyl-(m-cyano-phenyl)ethylamine. The final AcR5b-acylase preparation obtained in example 4d, which has been diluted 20 fold with 69 mM potassium phosphate buffer, pH 7, serve as the enzyme source. The Michaelis constants ($K_m$) and the maximum reaction velocities are calculated as described in example 9.

The $K_m$ values for (R)-N-acetyl-1-phenylethylamine and the racemic (m-cyano) derivative are 5.7 and 10.4 mM, the relative maximum reaction velocities are 100 and 23%, respectively.

Example 20

Isolation of Microorganisms with (S)-2-amino-1-phenyl-4-pentene Acylase Activity In general the procedure given in example 1 is applied with the following modifications:

74 Soil and water samples are used to inoculate enrichment cultures with pH 6, pH 7, and pH 9, incubated at 28° C., and with pH 7, incubated at 37° C.

The medium for the first propagation contains 0.5 g/l of sodium acetate as the sole carbon source, the medium for the second and third propagation 1 g/l of racemic 2-acetylamino-1-phenyl-4-pentene.

Strain cultivation is performed at the same temperature and pH used in the corresponding enrichment cultures.

The organisms from the enrichment cultures are isolated on Plate Count Agar (Fluka Co., Buchs, Switzerland).

The medium for growing the strains for the activity assays consists of 1 g/l of racemic 2-acetylamino-1-phenyl-4-pentene, 1 g/l yeast extract, and 1 g/l peptone in the mineral salt solution ML1. The incubation time for shake flask cultures is 48–72 h.

In order to test the activity and enantioselectivity of the acylase activity assays are performed with 5.47 mM of (S) and (R)-2-acetylamino-1-phenyl-4-pentene, respectively, as the substrate and 40 µl of crude cell extract as the enzyme source in a total volume of 400 µl. After an appropriate incubation time 200 µl of ice cooled acetone are mixed with 200 µl of the assay. 600 µl of 69 mM potassium phosphate buffer, pH 7, are added, and after centrifugation at 11500 rpm the concentration of 2-amino-1-phenyl-4-pentene in the supernatant is analyzed by HPLC (detection wavelength 210 nm).

18 organisms are isolated which hydrolyze preferentially one enantiomer of 2-acetylamino-1-phenyl-4-pentene, but only for one strain, *Rhodococcus globerulus* K1/1(=DSM 10337), exclusive cleavage of the (S)-enantiomer was observed in the enzyme assays.

Example 21

Growth and Induction of the Acylase of *Rhodococcus globerulus* K1/1 a) Variation of the Inducer

Strain K1/1 is grown in shake flask culture using the medium from example 21, but with 2 g/l of each yeast extract and peptone, with racemic 2-acetylamino-1-phenyl-4-pentene or alternatively racemic N-acetyl-1-phenylethylamine as the inducer in concentrations of 0, 4.92, 7.38, and 9.84 mM.

The measurement of the acylase activity and the O.D.660 reveals, that the acylase is only formed by strain K1/1 in the presence of an inducing substance, which can either be racemic 2-acetylamino-1-phenyl-4-pentene or racemic N-acetyl-1-phenylethylamine. Concentrations of 2-acetylamino-1-phenyl-4-pentene higher than 4.92 mM are inhibitory for the growth and the enzyme formation of strain K1/1. N-acetyl-1-phenylethylamine at concentrations of 7.38 and 9.84 mM, however, do not inhibit the growth, but neither leads to an increased cell density nor to an higher acylase yield ($U/l_{culture\ broth}$).

b) Variation of the Start pH-value and the Temperature

Strain K1/1 is grown in shake flasks (see example 21a) in the presence of 4.92 mM racemic 2-acetylamino-1-phenyl-4-pentene by varying the start pH-value between 4 and 9 in steps of 0.5 pH values at 28° C. and by varying the incubation temperature between 20 and 40° C. in steps of 5° C. at pH 7. After 72 h of incubation the O.D.660 and the acylase activity of the crude extracts are measured.

The best production of the acylase of *Rhodococcus globerulus* K1/1 is achieved at pH 6.5 and 30° C. (28 $U/l_{culture\ broth}$, 0.4 $U/mg_{protein\ in\ the\ crude\ extract}$).

Example 22

Enzymatic Hydrolysis with Highly Purified Acylase from *Arthrobacter aurescens* Ac5R To 10 ml of a 20 mM solution of each of the racemic amides shown below 1 in 0.1 M phosphate buffer pH 7.0, 5 ml (1.3 units) of the enzyme is added and the solutions are shaken at 100 rpm and 30° C.

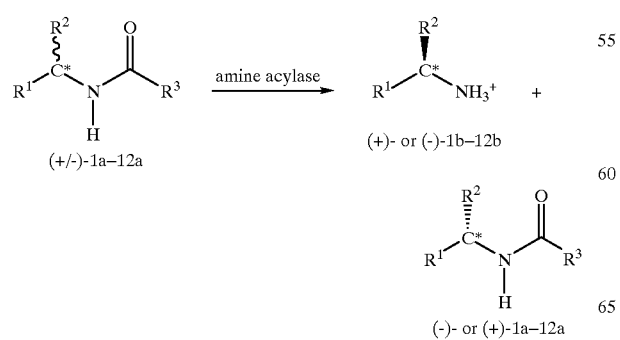

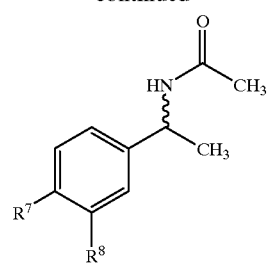

1a: $R^7$ = H, $R^8$ = H
2a: $R^7$ = H, $R^8$ = CN
3a: $R^7$ = CN, $R^8$ = H

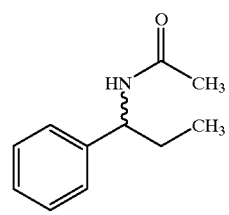

4a

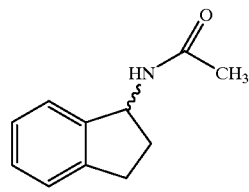

5a

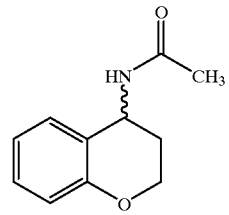

6a

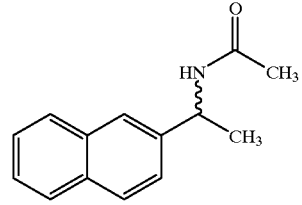

7a

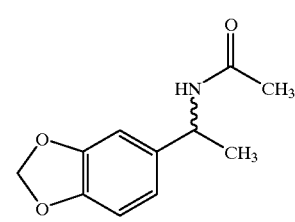

8a

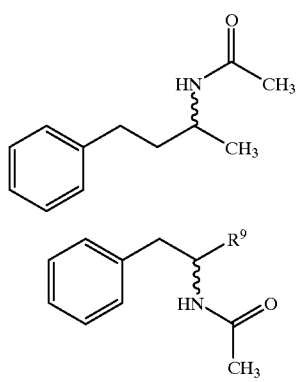

10a: R⁹ = —CH₂CH=CH₂
11a: R⁹ = —CH₂CH₂CH₃
12a: R⁹ = —CH₂CH₃

When the conversion reaches about 50% (checked by HPLC) the solutions are acidified to pH 2 by adding 1 N HCl and extracted three times with dichloromethane to obtain the unconverted amides. The aqueous layers are neutralized with 1 N NaOH solution and extracted again three times with dichloromethane to recover the formed amines. Both organic phases are dried with $MgSO_4$, filtered and the solvent is distilled off. The amides are used directly for optical purity determinations (HPLC), whereas the obtained amines are converted to the acetamides by adding 100 μl triethylamine and 100 μl acetic anhydride to each sample and then analyzed for the optical purity by "chiral" HPLC. The results are summarized in table 14.

TABLE 14

Conversion and enantioselectivity of the enzymatic hydrolysis with highly purified acylase from *Arthrobacter aurescens* Ac5R

| Substrate | Incubation time (h) | Conversion (%) | e.e. (S)-Amide | e.e. (R)-Amine | Selectivity E |
|---|---|---|---|---|---|
| 1a | 22 | 50.3 | >99.9 | 98.2 | >500 |
| 2a | 75 | 47.4 | 82.4 | 91.5 | 60 |
| 3a | 75 | 51.3 | >99.9 | 95.0 | 320 |
| 4a | 139 | 46.0 | 87.4 | >99.9 | >500 |
| 5a | 46 | 50.1 | 96.1 | 95.7 | 180 |
| 6a | 194 | 35.2 | 46.6 | 90.5 | 32 |
| 8a | 22 | 47.4 | 82.4 | 91.5 | 60 |

Example 23

Enzymatic Hydrolysis with Partially Purified Acylase from *Rhodococcus equi* Ac6

The experiments are carried out in the same manner as described in example 22. 200 ml (1.1 units) enzyme are used for each substrate listed in table 15.

TABLE 15

Conversion and enantioselectivity of the enzymatic hydrolysis with partially purified acylase from *Rhodococcus equi* Ac6

| Substrate | Incubation time (h) | Conversion (%) | e.e. (R)-Amide | e.e. (S)-Amine | Selectivity E |
|---|---|---|---|---|---|
| 1a | 18 | 50.6 | 99.3 | 96.8 | 350 |
| 2a | 19 | 46.1 | 85.5 | >99.9 | >500 |
| 3a | 19 | 49.4 | 97.4 | >99.9 | >500 |

TABLE 15-continued

Conversion and enantioselectivity of the enzymatic hydrolysis with partially purified acylase from *Rhodococcus equi* Ac6

| Substrate | Incubation time (h) | Conversion (%) | e.e. (R)-Amide | e.e. (S)-Amine | Selectivity E |
|---|---|---|---|---|---|
| 4a | 19 | 50.4 | >99.9 | 98.5 | >500 |
| 5a | 20 | 52.3 | 96.7 | 88.2 | 65 |
| 7a | 19 | 14.4 | 16.4 | 97.4 | 88 |
| 8a | 20 | 47.9 | 90.1 | 97.8 | 280 |
| 9a | 20 | 51.7 | >99.9 | 92.1 | 230 |

Example 24

Amide Hydrolysis with Whole Cells of *Rhodococcus globerulus* K1/1

To 50 ml of a 10 mM solution in phosphate buffer pH 7.0 of each racemic amide listed in table 16, whole cells of *Rhodococcus globerulus* K1/1 (each obtained from 50 ml shake flask medium (see example 21), $OD_{660}$=2.0) is added. The deacetylation is performed at 30° C. under continuous shaking (200 rpm). The reaction is monitored by HPLC and after the conversion is about 50% the reaction mixtures are worked up in the same manner as described in example 22. The results are summarized in table 16.

TABLE 16

Conversion and enantioselectivity of the enzymatic hydrolysis with whole cells of *Rhodococcus globerulus* K1/1

| Substrate | Incubation time (h) | Conversion (%) | e.e. (R)-Amide | e.e. (S)-Amine | Selectivity E |
|---|---|---|---|---|---|
| 1a | 3.0 | 50.6 | >99.9 | 97.5 | >500 |
| 4a | 3.5 | 52.6 | >99.9 | 90.0 | 140 |
| 6a | 3.5 | 51.7 | >99.9 | 93.5 | 290 |
| 10a | 3.5 | 51.7 | 95.7 | 90.0 | 70 |
| 11a | 4.0 | 55.7 | 97.8 | 77.8 | 35 |
| 12a | 2.0 | 49.4 | 90.7 | 93.0 | 87 |
| 12a | 3.5 | 53.1 | >99.9 | 87.9 | |

Example 25

Preparative Hydrolysis of Racemic 1a with Acylase from *Arthrobacter aurescens* Ac5R.

To 1 g (6.13 mmol) racemic N-acetyl 1-phenylethylamine (+/−)-1a, partially dissolved in 100 ml 0.1 M phosphate buffer pH 7.0, 100 ml (25.3 units) acylase from *Arthrobacter aurescens* Ac5R is added and the mixture is shaken (100 rpm) at 20° C. for 27 hours. After acidification (pH 2) by addition of HCl the reaction mixture is extracted three times with 100 ml dichloromethane. The combined organic layers are dried ($MgSO_4$) and the solvent is distilled off after filtration, yielding 0.496 g (49.6%) of (S)-N-acetyl 1-phenylethylamine (−)-1a ($[\alpha]^D_{20}$=−138.0° (c=1.0 EtOH), enantiomeric ratio S/R=96.8:3.2) as a white solid. The aqueous phase is neutralized by addition of $NaHCO_3$ and extracted again with dichloromethane. Usual workup leads to 0.323 g (43.5%) of (R)-1-phenylethylamine (+)-1b ($[\alpha]^D_{20}$=+29.4° (c=2.2 EtOH), enantiomeric ratio R/S=99.7:0.3) as colorless oil.

Example 26

Purification of the Acylase of *Rhodococcus globerulus* K1/1

26.1. Preparation of the crude extract in preparative scale. 100 ml of cell suspension (40% w/w) are poured into a 600 ml glass beaker and placed in a bucket of ice. The beaker has to remain in an ice bath during sonification. A one inch standard horn is used under the following conditions:
cycle time: 1 second
duty cycle: 50%
output control: 8
total sonification time: 20 minutes (without interruption)

After 20 minutes sonicating (40 minutes including interruption) the sample is centrifuged for 20 minutes at 9000 rpm in a Sorvall RC5B refrigerated (4° C.) superspeed centrifuge using a Sorvall GS-3 aluminum rotor. The supernatant is the crude extract.

The standard assay for K1/1-acylase activity used for monitoring the purification and for the enzymological characterization is performed by mixing 20 μl of an enzyme sample with 380 μl of a 5.55 mM solution of (S)-2-acetylamino-1-phenyl-4-pentene in 69 mM potassium phosphate buffer, pH 7, and incubating at 23° C. The dilution of the acylase and the incubation time are chosen so that not more than 1.3 mM of product are formed. The reaction is stopped by addition of 800 μl ice cold methanol. After centrifugation for 4 min at 11500 rpm in a Biofuge 15 (Heraeus Sepatech, Osterode, Germany) the supernatant is subjected to quantitative HPLC analysis (see example 1).

26.2. Nucleic acid precipitation.

3.25 ml of a 10% PEI solution (adjusted to pH 7.5 with 6N HCl) are added to 105 ml of cell homogenate (from sonification step) to reach a 0.3% concentration. The mixture is kept on ice for 30 minutes and gently stirred. Then the mixture is centrifuged for 20 minutes at 9000 rpm at 4° C. The supernatant is then used for ammonium sulfate precipitation.

26.3. Ammonium sulfate precipitation.

18.81 g of crystalline $(NH_4)_2SO_4$ are slowly added to 90 ml of crude extract after nucleic acid precipitation to reach a concentration of 35% saturation. The mixture is kept on ice for 30 minutes and gently stirred. Then the mixture is centrifuged for 20 minutes at 9000 rpm at 4° C. The supernatant is subjected to chromatography on an FPLC-system (Pharmacia, Uppsala, Sweden) for further purification.

26.4. FPLC.

Two different column types (hydrophobic interaction and gel filtration) coupled to the FPLC equipment are used to purify the acylase.

26.4.1. Hydrophobic interaction chromatography (HIC).

For HIC a Merck Fractogel TSK Butyl650(S) column (26×310 mm, volume: 165 ml) is prepared and equilibrated with a 35% saturated $(NH_4)_2SO_4$ solution (in phosphate buffer pH7.0). After loading the column with 90 ml of supernatant from the $(NH_4)_2SO_4$ precipitation the column is washed with 35% saturated $(NH_4)_2SO_4$ solution until no more protein is washed off the column. Then a $(NH_4)_2SO_4$ gradient spanning from 35% to 0% saturation with a total volume of 1150 ml is applied to the column. The flow is adjusted to 1.8 ml/min, fractions of 12 ml are collected and tested for acylase activity.

The acylase elutes between 11.5% and 7.5% $(NH_4)_2SO_4$. Active fractions are pooled (140 ml).

26.4.2. Ultrafiltration.

Concentration and desalination of the HIC fraction pool (140 ml) containing the *Rhodococcus globerulus* K1/1 acylase are performed in a CEC1 Amicon ultrafiltration chamber. A YM30 (MW cut off 30000 Da) membrane is utilized. Desalination is achieved by diafiltration and repeated additions of $(NH_4)_2SO_4$-free potassium phosphate buffer (69 mM, pH7.0) to the concentrated sample followed by a reconcentration step. The HIC fraction pool is concentrated to 4.5 ml.

26.4.3. Gel filtration.

A Pharmacia Superose 12HR 10/30 gel filtration column (10×300 mm) is utilized as the final purification step. The elution is performed using potassium phosphate buffer (69 mM, pH7.0) supplemented with 100 mM NaCl with a flow rate of 0.3 ml/min. 200 μl of the concentrated and desalted acylase fraction obtained from ultrafiltration are applied to the column. Fractions of 0.5 ml are collected and analyzed for the presence of acylase.

26.4.4. Purification scheme for the *Rhodococcus globerulus* K1/1 acylase.

| | volume (ml) | protein (mg/ml) | acylase (U) | spec. act. (U/mg) | yield (%) | purification factor |
|---|---|---|---|---|---|---|
| crude extract | 105 | 12.15 | 387.5 | 0.304 | 100 | 1.00 |
| PEI prec. | 90 | 9.92 | 309.6 | 0.347 | 79.9 | 1.14 |
| $NH_4SO_4$ prec. | 90 | 8.63 | 310.5 | 0.400 | 80.1 | 1.32 |
| HIC | 140 | 1.14 | 293.3 | 1.841 | 75.8 | 6.06 |
| gel filtration* | 33.8 | 2.36 | 251.7 | 3.174 | 65.0 | 10.44 |

*Only 200 ml of 4.5 ml concentrated and desalted HIC fraction (see Example 26.4.2) are applied to the *Pharmacia Superose* 12HR column. The data given in the table are calculated for the whole volume of the concentrated HIC fraction (4.5 ml).

Example 27

Characterization Data of the *Rhodococcus globerulus* K1/1 Acylase 27.1. Activity of the *Rhodococcus globerulus* K1/1 acylase in the presence of potential enzyme activators and inhibitors:

| group | compound | relative activity (%) | |
|---|---|---|---|
| | none | 100 | |
| | | 1 mM | 10 mM |
| metal cations | $CoCl_2$ | 97 | 86 |
| | $MnCl_2$ | 94 | 83 |
| | $ZnCl_2$ | 66 | 0 |
| | $MgCl_2$ | 101 | 87 |
| | $NiCl_2$ | 87 | 80 |
| | $CaCl_2$ | 89 | 85 |
| | $CuCl_2$ | 66 | 50 |
| | $FeCl_3$ | 101 | 37 |
| chelating agents | EDTA | 99 | 89 |
| | Na-citrate | 113 | 133 |
| thiol reducing agents | dithiothreitol | 112 | 77 |
| | mercaptoethanol | 106 | 101 |
| | glutathion, reduced | 104 | 93 |
| thiol group blocking agents | iodoacetamide | 104 | 67 |
| | p-hydroxy-mercuribenzoate | 89 | 96 |
| PLP-enzyme inhibitors | D-cycloserine | 104 | 96 |
| protease inhibitor | phenylmethylsulfonyl fluoride | 0.1 mM: 0% | 0.01 mM: 0% |

The K1/1-acylase is inhibited strongly only by 10 mM $Zn^{2+}$ and phenymethylsulfonylfluoride. The severe inhibition by the latter compound even at very low concentrations indicate a serine protease like reaction mechanism of the enzyme.

27.2. General characterization data of the *Rhodococcus globerulus* K1/1 acylase:

27.2.1. The molecular weight of the acylase is 54.6 kDa on SDS-PAGE (see example 4.c. and 5) and 92.3 kDa when subjected to gel filtration (see example 5) suggesting a homodimeric structure of the native acylase.

27.2.2. The isoelectric point of the acylase is measured as described in example 6 to be around pH 4.0.

27.2.3. For the determination of activity and stability of the acylase under varying pH conditions the following buffer solutions are utilized:

pH5.5–pH7.5 phosphate buffer
pH7.5–pH9.0 Tris buffer
pH9.0–pH10.5 glycine buffer For the determination of pH-stability acylase samples are incubated for 2 h at 23° C. in buffers of various pH. Then the enzyme samples are subjected to standard activity assays (see example 26).

The acylase shows a broad stability optimum between pH5.5 and pH7.5.

The activity of the K1/1-acylase is measured in standard activity assays (see example 26) under various pH conditions.

The acylase has an optimal activity between pH7.0 and pH7.5 with a sharper decrease of activity on the acidic side of the optimum.

27.2.4. Temperature stability of the *Rhodococcus globerulus* K1/1 acylase.

Samples of acylase are incubated at various temperatures ranging from 0° C. to 65° C. for 30 min. After cooling in an ice bath the acylase samples are subjected to standard activity assays (see example 26).

The acylase shows no loss of activity when incubated for 30 min at up to 50° C. Acylase incubated at 55° C. looses 40% of its activity whereas acylase incubated at higher temperatures (60° C., 65° C.) is fully inactivated within 30 min of incubation.

27.2.5. N-terminal amino acid sequence of the *Rhodococcus globerulus* K1/1 acylase For the determination of the N-terminal amino acid sequence of the K1/1-acylase a HP G1005A N-terminal Protein Sequencing Systems is utilized performing automated Edman degradation chemistry on protein samples retained on miniature adsorptive biphasic columns consisting of of a reverse-phase sample column mated to a strong anion exchange column. Analysis of PTH-amino acids is performed by an on-line HP1090 HPLC system (Hewlett Packard, Palo Alto, Calif., USA).

The N-terminal amino acid sequence (50 residues) is shown in SEQ ID NO 1: SQSEIVWASASELAARVRER-SLTPVEIGDAMIEHIDAVNPsINAVVQFDR.

Example 28

N-terminal Amino Acid Sequence of the (S)-N-acetyl-1-phenylethylamine Acylase of *Rhodococcus equi* Ac6

The determination of the N-terminal sequence is performed as described in example 27.2.5.

The N-terminal amino acid sequence (30 residues) of the Ac6-acylase is shown in SEQ ID NO 2: MNTSDPGWM-SATEMAAQVASKSLSPNEIAE.

Example 29

N-terminal Amino Acid Sequence of the (R)-specific Acylase of *Arthrobacter aurescens* AcR5b The determination of the N-terminal sequence is performed as described in example 27.2.5.

The N-terminal amino acid sequence of the small subunit (16 kDa) is shown in SEQ ID NO 3: PITNPA??RDHAE, the N-terminal amino acid sequence of the large subunit (89 kDa) is shown in SEQ ID NO 4: TAIrIrGY?DTPSVAPGE (?: amino acid unknown, small caps: amino acid not certain).

Example 30

Preparation of (S)-2-amino-1-phenyl-4-pentene Using the Purified K1/1 acylase

To 50 ml of a 10 mM solution of racemic 2-acetylamino-1-phenyl-4-pentene in phosphate buffer (pH 7.0) 7 ml of the K1/1 acylase are added (0.456 U), which has been purified by HIC and concentrated by ultrafiltration (example 26.5 and 26.6). The deacylation is performed at 30° C. under continuous shaking at 200 rpm. The reaction is monitored by HPLC (see example 1), and after the conversion is about 50% the solution is acidified to pH 2 with 1 N HCl and extracted three times with one volume of dichloromethane to obtain the unconverted amides. The aqueous phase is neutralized with 1 N NaOH and extracted again three times with dichloromethane to recover the formed amines. Both organic phases are dried with $MgSO_4$, filtered and the solvent is distilled off. The amides are used directly for optical purity determinations via HPLC under the following conditions: Chiralcel OJ column, hexane/isopropanol 9:1 as the eluent, flow rate 1 ml/min., detection at 208 nm. The obtained amines are converted to the acetamides by adding 100 ml triethylamine and 100 ml acetic anhydride to each sample before being also analyzed for the optical purity by HPLC.

At 50.3% conversion (S)-2-amino-1-phenyl-4-pentene is obtained with 87.4% ee, (R)-N-2-acetylamino-1-phenyl-4-pentene with 98.8% ee, corresponding to an E-value of 74.9%.

Example 31

Preparation of (S)-2-amino-1(4-chlorophenyl)-4-pentene Using the K1/1-acylase in Form of Whole Cells of *Rhodococcus globerulus* K1/1

Strain K1/1 is grown according to example 3 in a 30 l fermenter filled with 20 l of basic medium containing 1 g/l of racemic N-acetyl-1-phenylethylamine. The cells are harvested by continuous centrifugation and resuspended in the reaction mixture, which is prepared by adding a solution of 80 g racemic 2-acetylamino-1(4-chlorophenyl)-4-pentene in 500 ml methanol to 20 l of potassium phosphate buffer, 69 mM, pH 7. After stirring for 21 h at 28° C. and 500 rpm the amine formed and the unreacted amide are separated and analyzed for their optical purity analogously to the procedure given in example 30.

31.1 g (94.5% yield) of (S)-2-amino-1(4-chlorophenyl)-4-pentene with >99.9% ee and 38.6 g (97% yield) of (R)-2-acetylamino-1(4-chlorophenyl)-4-pentene with 98.5% ee are isolated.

DEPOSITION OF MICROORGANISMS

The following microorganisms are deposited according to the Budapest Treaty with the DSM—Deutsche Sammlung von Mikroorganismen und Zellkulturen GmbH, Mascheroder Weg 1b, D-38124 Braunschweig:

*Rhodococcus globerulus* K1/1, DSM 10337 (deposited Sep. 23, 1995)

*Rhodococcus equi* Ac6, DSM 10278 (deposited Sep. 23, 1995)

*Arthrobacter aurescens* AcR5b, DSM 10280 (deposited Sep. 23, 1995)

What is claimed is:

1. A purified biocatalyst isolated from a microorganism selected from the group consisting of *Rhodococcus globerulus, Rhodococcus equi* and *Arthrobacter aurescens*, wherein the biocatalyst exhibits amine acylase enzymatic activity without lipase- or esterase-activity, and wherein the biocatalyst stereoselectively hydrolyses a racemic acylamide of formula (1)

(1)

wherein $R^2$ is aryl or $C_1$–$C_4$aryl; or $R^1$ and $R^2$ together are forming a 5 to 7 membered ring substituted by or fused to aryl;

$R^3$ is an aliphatic acyl residue; and $R^1$ and $R^3$ together are chosen in order to form a compound of formula (1) that is not a derivative of a natural amino acid; wherein each of the residues can be substituted or unsubstituted.

2. A purified biocatalyst exhibiting amine acylase enzymatic activity without lipase- or esterase-activity, wherein the biocatalyst stereoselectively hydrolyses a racemic acylamide of formula (1)

(1)

wherein $R^2$ is aryl or $C_1$–$C_4$aryl; or $R^1$ and $R^2$ together are forming a 5 to 7 membered ring substituted by or fused to aryl;

$R^3$ is an aliphatic acyl residue; and $R^1$ and $R^3$ together are chosen in order to form a compound of formula (1) that is not a derivative of a natural amino acid; wherein each of the residues can be substituted or unsubstituted, wherein the biocatalyst comprises an amino acid sequence selected from the group consisting of SEQ ID Nos 1, 2, 3 and 4.

3. A process comprising the hydrolysis of a racemic N-acylamide acylamide which has an aliphatic acyl residue and which is not a derivative of a natural amino acid, characterized in that a biocatalyst according to claim 1 is used.

4. The process according to claim 3, which has the following reaction scheme, (A)

whereby in the formula (1) to (4)

$R^1$ is $C_1$–$C_8$alkyl, $C_2$–$C_8$alkenyl, $C_1$–$C_6$alkoxy, $C_2$–$C_6$alkylcarboxy or carboxy;

$R^2$ is aryl or $C_1$–$C_4$aryl; unsubstituted or substituted by $C_1$–$C_4$alkyl, $C_1$–$C_4$alkoxy, $C_1$–$C_4$hydroxyalkyl, $C_1$–$C_4$Aminoalkyl, $C_1$–$C_4$haloalkyl, hydroxy, amino, halogeno, nitro or sulfo, cayno;

or wherein $R_1$ and $R_2$ together are forming a 5 to 7 membered ring substituted by aryl, wherein the ring may contain one or two heteroatoms selected from nitrogen, sulfur and oxygen; and substituted by or fused to aryl;

$R^3$ is an aliphatic acyl residue.

5. The process of claim 3 in which the aliphatic residue is methyl if the biocatalyst is derived from *Arthrobacter aurescens* AcR5b, DSM 10280.

6. The process of claim 3 in which the biocatalyst is used in immobilized form.

7. The process of claim 3 wherein the pH is from 5.5 to 10.5 and the temperature is from 10 to 65° C.

8. The biocatalyst of claim 1, wherein the microorganism is selected from the group consisting of *Rhodococcus globerulus* K1/1, DSM 10337, *Rhodococcus equi* Ac6, DSM 10278 and *Arthrobacter aurescens* AcR5b, DSM 10289.

* * * * *

UNITED STATES PATENT AND TRADEMARK OFFICE
CERTIFICATE OF CORRECTION

PATENT NO. : 6,235,516 B1
DATED : May 22, 2001
INVENTOR(S) : Ghisalba et al.

It is certified that error appears in the above-identified patent and that said Letters Patent is hereby corrected as shown below:

Column 41, claim 1,
Structural formula should read:

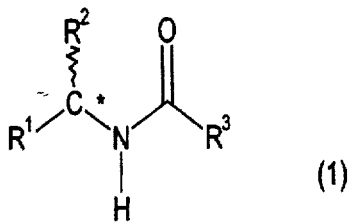

(1)

Column 41, claim 2,
Structural formula should read:

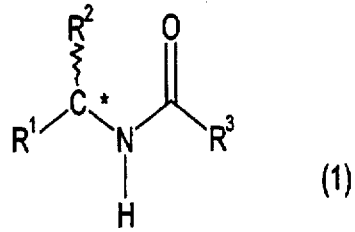

(1)

Column 42, claim 4,
Structural formula should read:

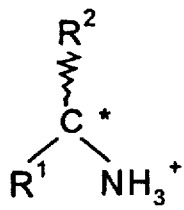

R- (or S) amine (2)

UNITED STATES PATENT AND TRADEMARK OFFICE
CERTIFICATE OF CORRECTION

PATENT NO.   : 6,235,516 B1
DATED        : May 22, 2001
INVENTOR(S)  : Ghisalba et al.

It is certified that error appears in the above-identified patent and that said Letters Patent is hereby corrected as shown below:

<u>Column 42, claim 4,</u>
Line 36, should read -- $R_1$ is hydrogen, $C_1$-$C_8$alkyl, $C_2$-$C_8$alkenyl, $C_1$-$C_8$alkozy, --.
Line 37, should read -- $C_2$-$C_8$alkylcarboxy or carboxy; --.

Signed and Sealed this

Fifth Day of February, 2002

Attest:

JAMES E. ROGAN
*Director of the United States Patent and Trademark Office*

*Attesting Officer*

SEQUENCE LISTING

<160> NUMBER OF SEQ ID NOS: 4

<210> SEQ ID NO: 1
<211> LENGTH: 50
<212> TYPE: PRT
<213> ORGANISM: Rhodococcus globerulus
<220> FEATURE:
<221> NAME/KEY: UNSURE
<222> LOCATION: (41)..
<223> OTHER INFORMATION: amino acid is uncertain

<400> SEQUENCE: 1

Ser Gln Ser Glu Ile Val Trp Ala Ser Ala Ser Glu Leu Ala Ala Arg
 1               5                  10                  15

Val Arg Glu Arg Ser Leu Thr Pro Val Glu Ile Gly Asp Ala Met Ile
            20                  25                  30

Glu His Ile Asp Ala Val Asn Pro Ser Ile Asn Ala Val Val Gln Phe
        35                  40                  45

Asp Arg
    50

<210> SEQ ID NO: 2
<211> LENGTH: 30
<212> TYPE: PRT
<213> ORGANISM: Rhodococcus equi

<400> SEQUENCE: 2

Met Asn Thr Ser Asp Pro Gly Trp Met Ser Ala Thr Glu Met Ala Ala
 1               5                  10                  15

Gln Val Ala Ser Lys Ser Leu Ser Pro Asn Glu Ile Ala Glu
            20                  25                  30

<210> SEQ ID NO: 3
<211> LENGTH: 13
<212> TYPE: PRT
<213> ORGANISM: Arthrobacter aurescens
<220> FEATURE:
<221> NAME/KEY: UNSURE
<222> LOCATION: (7)..(8)
<223> OTHER INFORMATION: amino acids are unknown

<400> SEQUENCE: 3

Pro Ile Thr Asn Pro Ala Xaa Xaa Arg Asp His Ala Glu
 1               5                  10

<210> SEQ ID NO: 4
<211> LENGTH: 18
<212> TYPE: PRT
<213> ORGANISM: Arthrobacter aurescens
<220> FEATURE:
<221> NAME/KEY: UNSURE
<222> LOCATION: (4)..
<223> OTHER INFORMATION: amino acid is uncertain
<220> FEATURE:
<221> NAME/KEY: UNSURE
<222> LOCATION: (6)..
<223> OTHER INFORMATION: amino acid is uncertain
<220> FEATURE:
<221> NAME/KEY: UNSURE
<222> LOCATION: (9)..
<223> OTHER INFORMATION: amino acid is unknown

```
-continued

<400> SEQUENCE: 4

Thr Ala Ile Arg Ile Arg Gly Tyr Xaa Asp Thr Pro Ser Val Ala Pro
 1               5                  10                  15
Gly Glu
```